(12) United States Patent
Clark et al.

(10) Patent No.: US 9,321,736 B2
(45) Date of Patent: *Apr. 26, 2016

(54) PYRIMIDINE CYCLOHEXYL GLUCOCORTICOID RECEPTOR MODULATORS

(71) Applicant: Corcept Therapeutics, Inc., Menlo Park, CA (US)

(72) Inventors: Robin Clark, Kaleheo, HI (US); George Hynd, Harlow (GB); Nicholas Ray, Harlow (GB); Mohammad Sajad, Harlow (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,719

(22) Filed: Nov. 7, 2014

(65) Prior Publication Data

US 2015/0065532 A1 Mar. 5, 2015

Related U.S. Application Data

(63) Continuation of application No. 14/179,960, filed on Feb. 13, 2014, now Pat. No. 8,906,917, which is a continuation of application No. 13/422,399, filed on Mar. 16, 2012, now Pat. No. 8,685,973.

(60) Provisional application No. 61/464,289, filed on Mar. 18, 2011.

(51) Int. Cl.

| | | |
|---|---|---|
| C07D 239/02 | (2006.01) |
| C07D 239/54 | (2006.01) |
| C07D 213/55 | (2006.01) |
| C07D 213/74 | (2006.01) |
| C07D 239/26 | (2006.01) |
| C07D 239/553 | (2006.01) |
| C07D 239/56 | (2006.01) |
| C07D 277/30 | (2006.01) |
| C07D 401/06 | (2006.01) |
| C07D 417/06 | (2006.01) |
| C07D 239/22 | (2006.01) |
| C07D 403/06 | (2006.01) |
| C07D 413/06 | (2006.01) |
| C07F 7/18 | (2006.01) |
| C07D 239/545 | (2006.01) |
| C07D 417/08 | (2006.01) |

(52) U.S. Cl.
CPC ............ *C07D 239/54* (2013.01); *C07D 213/55* (2013.01); *C07D 213/74* (2013.01); *C07D 239/22* (2013.01); *C07D 239/26* (2013.01); *C07D 239/545* (2013.01); *C07D 239/553* (2013.01); *C07D 239/56* (2013.01); *C07D 277/30* (2013.01); *C07D 401/06* (2013.01); *C07D 403/06* (2013.01); *C07D 413/06* (2013.01); *C07D 417/06* (2013.01); *C07D 417/08* (2013.01); *C07F 7/1852* (2013.01)

(58) Field of Classification Search
USPC .................................. 514/235.8; 544/309
See application file for complete search history.

(56) References Cited

U.S. PATENT DOCUMENTS

| | | | |
|---|---|---|---|
| 6,852,719 B2 | 2/2005 | Liu et al. | |
| 7,576,076 B2 | 8/2009 | Clark et al. | |
| 7,799,782 B2 | 9/2010 | Munson et al. | |
| 8,173,664 B2 | 5/2012 | Clark et al. | |
| 8,685,973 B2 * | 4/2014 | Clark et al. | 514/235.8 |
| 8,906,917 B2 | 12/2014 | Clark et al. | |

FOREIGN PATENT DOCUMENTS

| | | |
|---|---|---|
| EP | 0037495 | 10/1981 |
| EP | 0369627 | 5/1990 |
| EP | 0722732 | 7/1996 |
| JP | 06128238 | 5/1994 |
| JP | 10017555 | 1/1998 |
| WO | 02/44120 | 6/2002 |
| WO | 03/084935 | 10/2003 |

OTHER PUBLICATIONS

International Search Report and Written Opinion dated Dec. 13, 2005, issued in related International Patent Appln. No. PCT/US2005/023675, filed Jun. 26, 2005.

International Search Report and Written Opinion dated Jun. 27, 2012, issued in related International Patent Appln. No. PCT/US2012/29376, filed Mar. 16, 2012.

Bhuyan, Pulak J., et al., "Studies on Uracils: Synthesis of Novel Uracil Analogs via 1, 5- and 1, 6-Intramolecular Cycloadditional Reactions", XP002355359; Database CA 'Online'; Chemical Abstracts Service, Columbus, OH, US; Database Accession No. 1998:598911, Abstract.

Bledsoe, et al., "Crystal Structure of the Glucocorticoid Receptor Ligand Binding Domain Reveals a Novel Mode of Receptor Dimerization and Coactivator Recognition," 2002, Cell. vol. 110, pp. 93-105.

Dorwald, F.A., *Side Reactions in Organic Synthesis*, 2005, Wiley, VCH, Weinheim p. IX of Preface.

Fukazawa, Nobuyuki, et al., "6-Amino-5-Methyluracil Derivativies and Their Use as Thymidine Phosphorylase Inhibitors and Neovascularization Inhibitors", XP002355358; Database CA 'Online'; Chemical Abstracts Service, Columbus, OH, US; Database Accession No. 1998:59356, Abstract.

Teutsch, G., et al., "Design of Ligands for the Glucocorticoid and Progestin Receptors", Biochemical Society Transactions (1991) 19(4):901-908.

* cited by examiner

*Primary Examiner* — Rei-Tsang Shiao

(74) *Attorney, Agent, or Firm* — Kilpatrick Townsend and Stockton LLP

(57) ABSTRACT

The present invention provides a class of pyrimidinedione cyclohexyl compounds and methods of using these compounds as glucocorticoid receptor modulators.

6 Claims, 1 Drawing Sheet

PYRIMIDINE CYCLOHEXYL GLUCOCORTICOID RECEPTOR MODULATORS

CROSS-REFERENCES TO RELATED APPLICATIONS

This application is a continuation of U.S. application Ser. No. 14/179,960, filed Feb. 13, 2014, which is a continuation of U.S. Pat. No. 8,658,973, filed Mar. 16, 2012, which claims priority to U.S. Provisional Application No. 61/454,289, filed Mar. 18, 2011, which is incorporated in its entirety herein for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which differs in only the last fifteen amino acids. The two types of GR have high affinity for their specific ligands, and are considered to function through the same transduction pathways.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

In addition to cortisol, the biological effects of other steroids can be modulated at the GR level using receptor modulators, such as agonists, partial agonists and antagonists. When administered to subjects in need thereof, steroids can provide both intended therapeutic effects, e.g., by stimulating glucocorticoid receptor transrepression, as well as negative side effects, e.g. by chronic glucocorticoid receptor transactivation. What is needed in the art are new compositions and methods for modulating GR receptors. Surprisingly, the present invention meets these and other needs.

BRIEF SUMMARY OF THE INVENTION

In one embodiment, the present invention provides a compound of formula I:

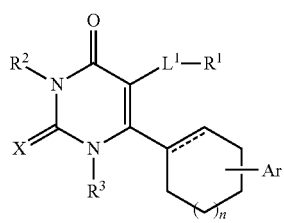

(I)

wherein the dashed line is absent or a bond. X is O or S. $R^1$ is cycloalkyl, heterocycloalkyl, aryl or heteroaryl, optionally substituted with from 1 to 3 $R^{1a}$ groups. Each $R^{1a}$ is independently H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloalkoxy, $-OR^{1b}$, $-NR^{1b}R^{1c}$, $-C(O)R^{1b}$, $-C(O)OR^{1b}$, $-OC(O)R^{1b}$, $-C(O)NR^{1b}R^{1c}$, $-NR^{1b}C(O)R^{1c}$, $-SO_2R^{1b}$, $-SO_2NR^{1b}R^{1c}$, cycloalkyl, heterocycloalkyl, aryl or heteroaryl. $R^{1b}$ and $R^{1c}$ are each H or $C_{1-6}$ alkyl. $R^2$ is H, $C_{1-6}$ alkyl, $C_{1-6}$ alkyl-$OR^{1b}$, $C_{1-6}$ alkyl-$NR^{1b}R^{1c}$ or $C_{1-6}$ alkylene-heterocycloalkyl. $R^3$ is H or $C_{1-6}$ alkyl. Ar is aryl, optionally substituted with 1-4 $R^4$ groups. Each $R^4$ is H, $C_{1-6}$ alkyl, $C_{1-6}$ alkoxy, halogen, $C_{1-6}$ haloalkyl or $C_{1-6}$ haloalkoxy. $L^1$ is a bond or $C_{1-6}$ alkylene. Subscript n is an integer from 0 to 3. Also included are the salts and isomers of the compounds recited herein.

In a second embodiment, the present invention provides a pharmaceutical composition including a pharmaceutically acceptable excipient and a compound of formula I.

In a third embodiment, the present invention provides a method of treating a disorder or condition through modulating a glucocorticoid receptor, the method including administering to a subject in need of such treatment, a therapeutically effective amount of a compound of formula I, thereby treating the disorder or condition.

In a fourth embodiment, the present invention provides a method of treating a disorder or condition through antagonizing a glucocorticoid receptor, the method including administering to a subject in need of such treatment, an effective amount of a compound of formula I.

DETAILED DESCRIPTION OF THE INVENTION

I. General

Figure 1:
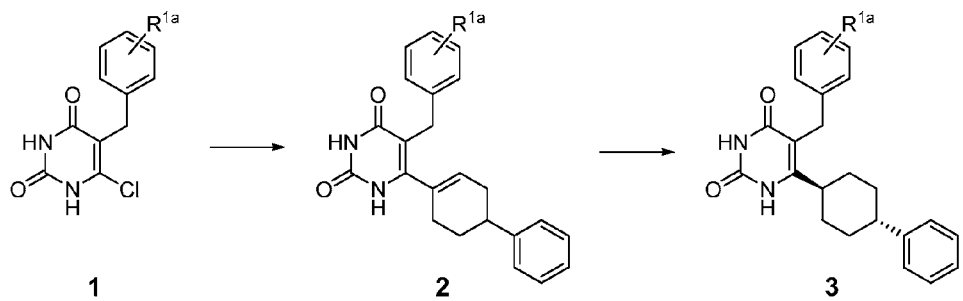
FIG. 1 shows a method of making the compounds of the present invention.

The present invention provides compounds capable of modulating a glucocorticoid receptor (GR) and thereby providing beneficial therapeutic effects. The compounds include benzyl pyrimidinedione-cyclohexyl-phenyls. The present invention also provides methods of treating diseases and disorders by modulating a GR receptor with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

As used herein, the term "alkylene" refers to either a straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$CH((CH_2)_nCH_3)$—, wherein n=0-5.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

As used herein, the term "alkoxy" refers to an alkyl radical as described above which also bears an oxygen substituent capable of covalent attachment to another hydrocarbon for example, methoxy, ethoxy or t-butoxy group.

As used herein, the term "halogen," by itself or as part of another substituent, means, unless otherwise stated, a fluorine, chlorine, bromine, or iodine atom.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluoromethane refers to 1,1,1-trifluoromethyl.

As used herein, the term "haloalkoxy" refers to alkoxy as defined above where some or all of the hydrogen atoms are substituted with halogen atoms. "Haloalkoxy" is meant to include monohaloalkyl(oxy) and polyhaloalkyl(oxy).

As used herein, the term "alkylamine" refers to an alkyl groups as defined within, having one or more amino groups. The amino groups can be primary, secondary or tertiary. The alkyl amine can be further substituted with a hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_3$-$C_8$ cycloalkyl includes cyclopropyl, cyclobutyl, cyclopentyl, cyclohexyl, cycloheptyl, and cyclooctyl. Cycloalkyl also includes norbornyl and adamantyl.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "alkylene-heterocycloalkyl" refers to a heterocycloalkyl group, as defined above, which is linked to another group by an alkylene. The heterocycloalkyl and the group to which the heterocycloalkyl is linked by an alkylene can be linked to the same atom or different atom of the alkylene.

As used herein, the term "aryl" means, unless otherwise stated, a polyunsaturated, aromatic, hydrocarbon substituent which can be a single ring or multiple rings (preferably from 1 to 3 rings) which are fused together or linked covalently. Examples include, but are not limited to, phenyl, biphenyl, naphthyl, and benzyl.

As used herein, the term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like). Likewise, the term "heteroarylalkyl" is meant to include those radicals in which a heteroaryl group is attached to an alkyl group.

Each of the above terms (e.g., "alkyl," "aryl" and "heteroaryl") are meant to include both substituted and unsubstituted forms of the indicated radical. Examples of substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR'C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NR(SO$_2$)R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the present invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R''', —OC(O)R', —C(O)R', —CO$_2$R', —CONR'R", —OC(O)NR'R", —NR'C(O)R', —NR'—C(O)NR"R''', —NR'C(O)$_2$R', —NR—C(NR'R"R''')=NR'''', —NR—C(NR'R")=NR''', —S(O)R', —S(O)$_2$R', —S(O)$_2$NR'R", —NR(SO$_2$)R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the present invention includes more than one R group, for example, each of the R groups is independently selected as are each R', R", R''' and R'''' groups when more than one of these groups is present.

Where two substituents are "optionally joined together to form a ring," the two substituents are covalently bonded together with the atom or atoms to which the two substituents are joined to form a substituted or unsubstituted aryl, a substituted or unsubstituted heteroaryl, a substituted or unsubstituted cycloalkyl, or a substituted or unsubstituted heterocycloalkyl ring.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Hydrate" refers to a compound that is complexed to at least one water molecule. The compounds of the present invention can be complexed with from 1 to 10 water molecules.

"Isomers" refers to compounds with the same chemical formula but which are structurally distinguishable.

"Tautomer" refers to one of two or more structural isomers which exist in equilibrium and which are readily converted from one form to another.

As used herein, the phrases "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the terms "treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

As used herein, the terms "disorder" or "condition" refer to a state of being or health status of a patient or subject capable of being treated with the glucocorticoid receptor modulators of the present invention. Examples of disorders or conditions include, but are not limited to, obesity, hypertension, depression, anxiety, and Cushing's Syndrome.

As used herein, the phrase "glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

As used herein, the term "modulating a glucocorticoid receptor" refers to methods for adjusting the response of a glucocorticoid receptor towards glucocorticoids, glucocorticoid antagonists, agonists, and partial agonists. The methods include contacting a glucocorticoid receptor with an effective amount of either an antagonist, an agonist, or a partial agonist and detecting a change in GR activity.

As used herein, the term "glucocorticoid receptor modulator" refers to any composition or compound which modulates the binding of a glucocorticoid receptor (GR) agonist, such as cortisol, or cortisol analogs, synthetic or natural, to a GR. The modulation can include partially or completely inhibiting (antagonizing) the binding of a GR agonist to a GR. A "specific glucocorticoid receptor antagonist" refers to any composition or compound which inhibits any biological response associated with the binding of a GR to an agonist. By "specific," we intend the drug to preferentially bind to the GR rather than other nuclear receptors, such as mineralocorticoid receptor (MR) or progesterone receptor (PR). GR modulators of the present invention include compounds of Formula I below.

As used herein, the term "antagonizing" refers to blocking the binding of an agonist at a receptor molecule or to inhibiting the signal produced by a receptor-agonist. A receptor antagonist blocks or dampens agonist-mediated responses.

As used herein, the terms "patient" or "subject" refers to a living organism suffering from or prone to a condition that can be treated by administration of a pharmaceutical composition as provided herein. Non-limiting examples include humans, other mammals and other non-mammalian animals.

As used herein, the phrase "therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

The terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substitutent group, the compound is substituted with at least one substituent group, wherein each substitutent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

In some embodiments, the present invention provides a compound of formula I:

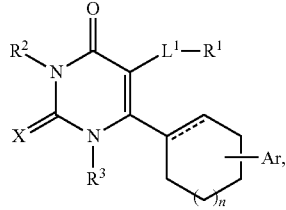
(I)

wherein the dashed line is absent or a bond. X is O or S. $R^1$ is cycloalkyl, heterocycloalkyl, aryl or heteroaryl, optionally substituted with from 1 to 3 $R^{1a}$ groups. Each $R^{1a}$ is independently H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloloxy, —$OR^{1b}$, —$NR^{1b}R^{1c}$, —$C(O)R^{1b}$, —$C(O)OR^{1b}$, —$OC(O)R^{1b}$, —$C(O)NR^{1b}R^{1c}$, —$NR^{1b}C(O)R^{1c}$, —$SO_2R^{1b}$, —$SO_2NR^{1b}R^{1c}$, cycloalkyl, heterocycloalkyl, aryl or heteroaryl. $R^{1b}$ and $R^{1c}$ are each H or $C_{1-6}$ alkyl. $R^2$ is H, $C_{1-6}$ alkyl, $C_{1-6}$ alkyl-$OR^{1b}$, $C_{1-6}$ alkyl-$NR^{1b}R^{1c}$ or $C_{1-6}$ alkylene-heterocycloalkyl. $R^3$ is H or $C_{1-6}$ alkyl. Ar is aryl, optionally substituted with 1-4 $R^4$ groups. Each $R^4$ is H, $C_{1-6}$ alkyl, $C_{1-6}$ alkoxy, halogen, $C_{1-6}$ haloalkyl or $C_{1-6}$ haloalkoxy. $L^1$ is a bond or $C_{1-6}$ alkylene. Subscript n is an integer from 0 to 3. Also included are the salts and isomers of the compounds recited herein.

In some other embodiments, the present invention provides a compound having formula Ia:

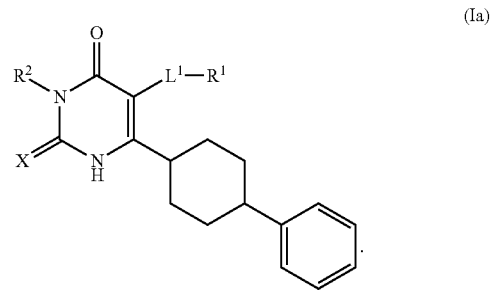
(Ia)

In some embodiments, $L^1$ is methylene. In other embodiments, Ar is phenyl.

In some embodiments, the present invention provides a compound having formula Ib:

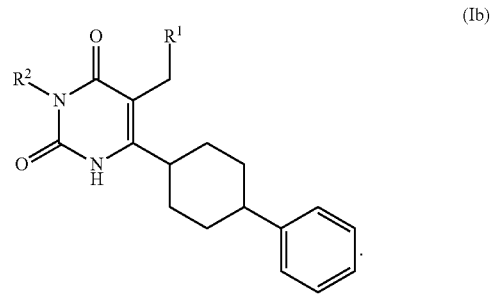
(Ib)

In some other embodiments, the present invention provides a compound having formula Ic:

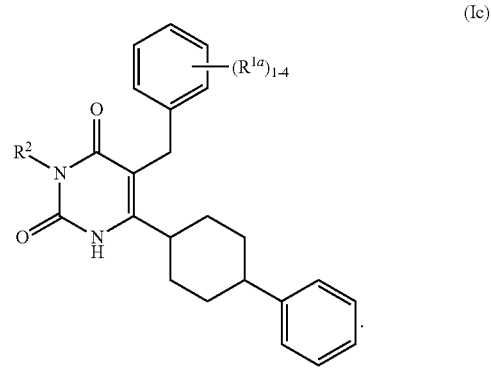
(Ic)

In some embodiments, the present invention provides a compound wherein $R^1$ is aryl or heteroaryl. In other embodiments, $R^1$ is selected from the group consisting of phenyl, pyridyl, pyrimidine, and thiazole. In some other embodiments, each $R^{1a}$ is independently H, $C_{1-6}$ alkyl, $C_{1-6}$ alkoxy, halogen, $C_{1-6}$ haloalkyl, —$NR^{1b}R^{1c}$, or —$SO_2R^{1b}$. In still other embodiments, each $R^{1a}$ is $C_{1-6}$ haloalkyl. In some other embodiments, each $R^{1a}$ is independently H, Me, Et, —OMe, F, Cl, —CF$_3$, —NMe$_2$, or —SO$_2$Me. In other embodiments, each R$^{1a}$ is —CF$_3$. In some other embodiments, R$^2$ is H or C$_{1-6}$ alkyl. In other embodiments, R$^2$ is H.
In some embodiments, the present invention provides a compound selected from the following:
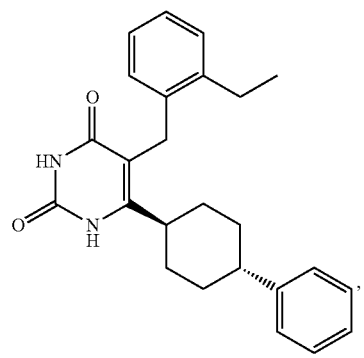
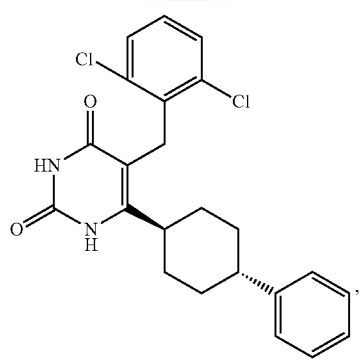
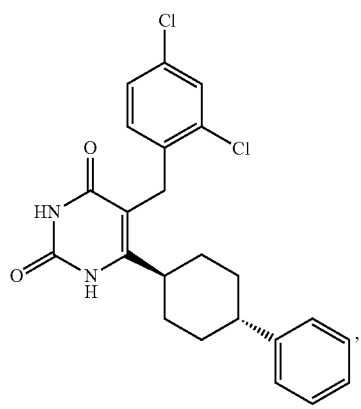
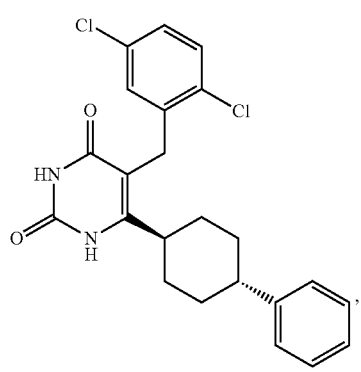
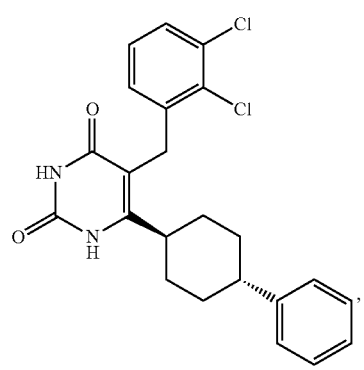
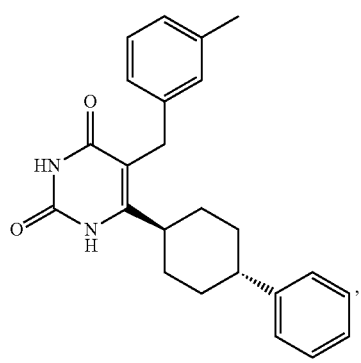

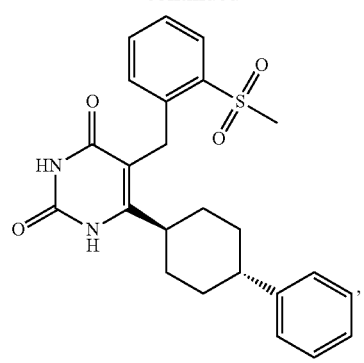
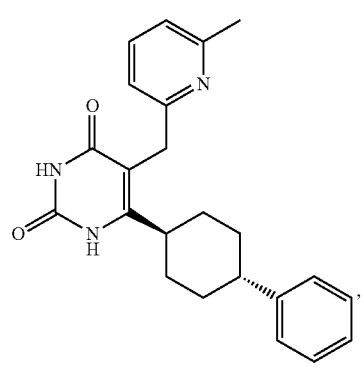
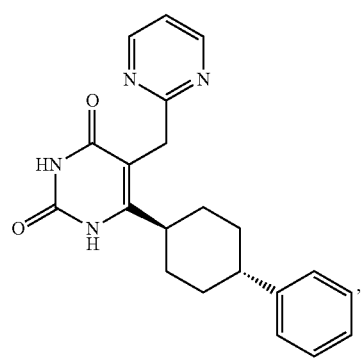
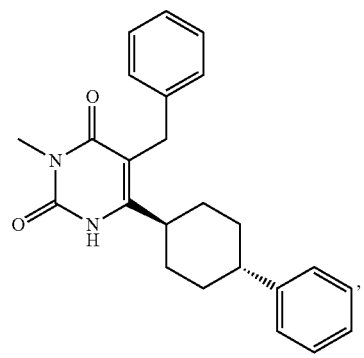
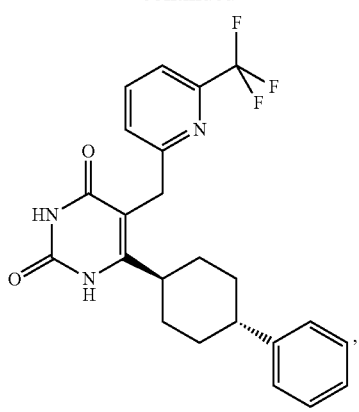
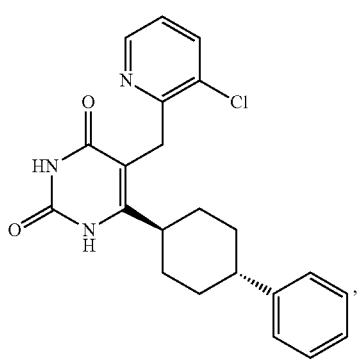
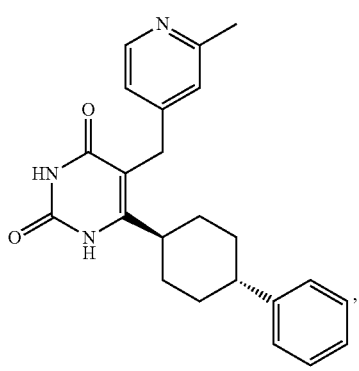
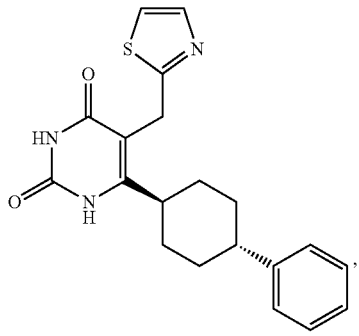

-continued
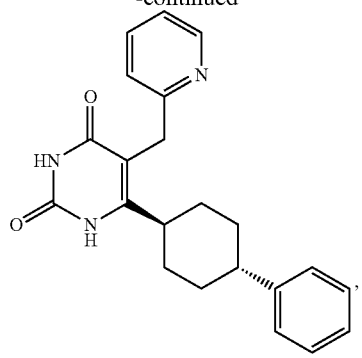
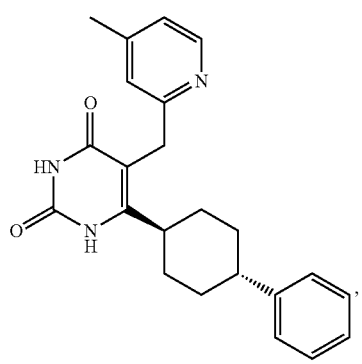
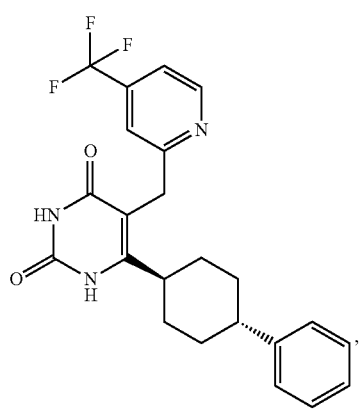
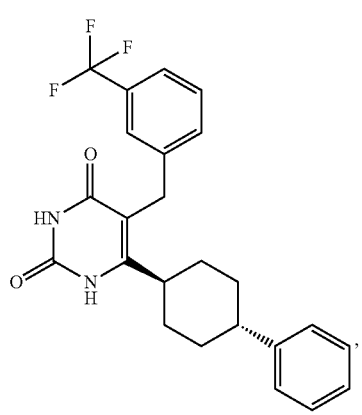
-continued
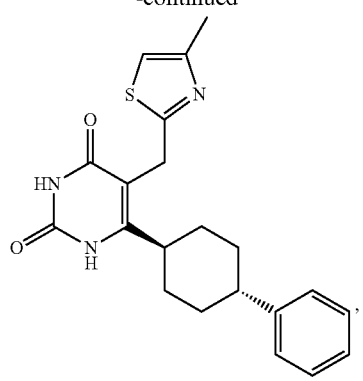
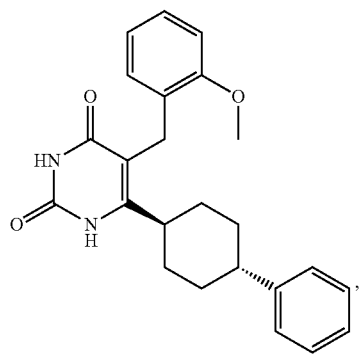
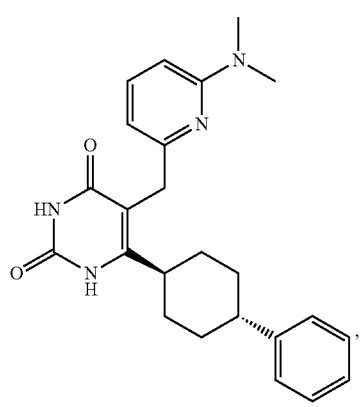
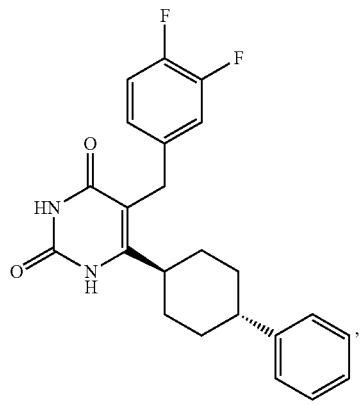

15
-continued
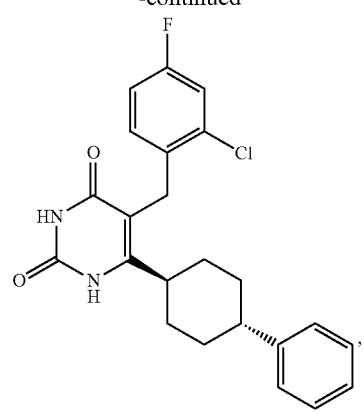
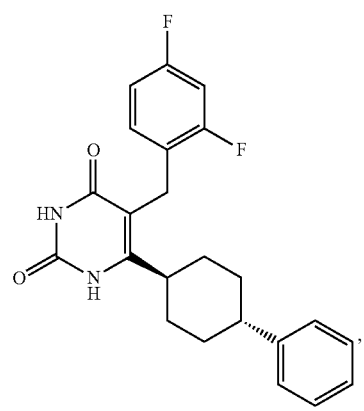
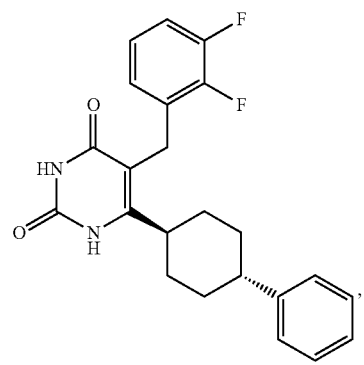
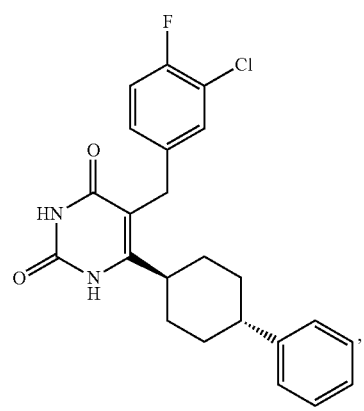
16
-continued
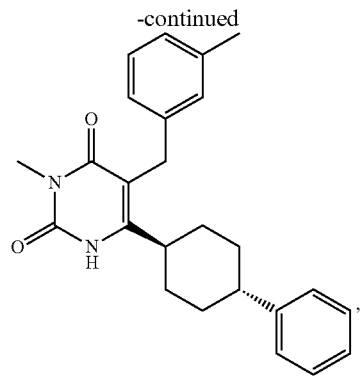
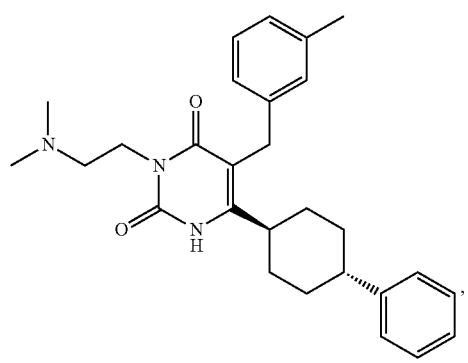
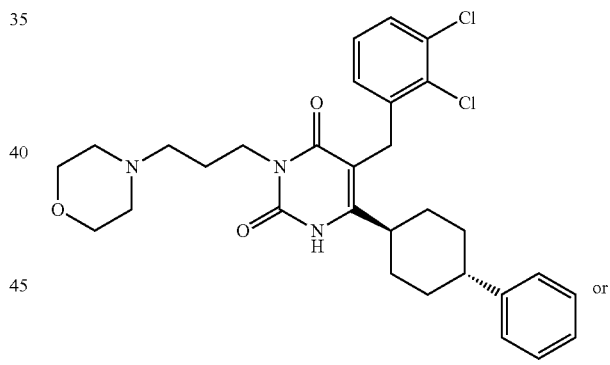
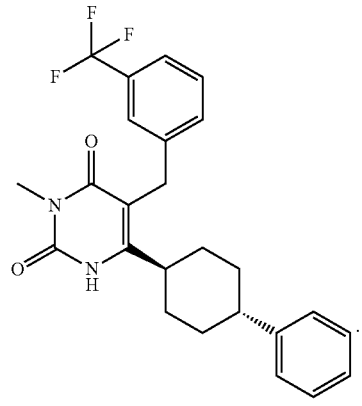

In some other embodiments, the present invention provides a compound having the formula:

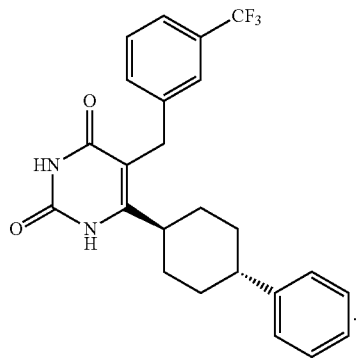 [SMILES: O=c1[nH]c(=O)c(Cc2cccc(C(F)(F)F)c2)c([C@H]2CC[C@H](c3ccccc3)CC2)[nH]1]

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center.

Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the present invention can be prepared by a variety of methods known in the art. For example, the compounds can be prepared as shown in FIG. 1. In FIG. 1, the chloro-pyrimidinediones 1 (described in WO06/014394 and incorporated herein) are coupled with a 4-phenylcyclohex-1-enyl boronate ester in the presence of a Pd catalyst to afford the cyclohexenyl pryimidinediones 2. Catalytic hydrogenation then affords a cis/trans mixture from which the desired trans-isomer 3 can be obtained by conventional separation techniques, e.g., column chromatography.

Figure 2:
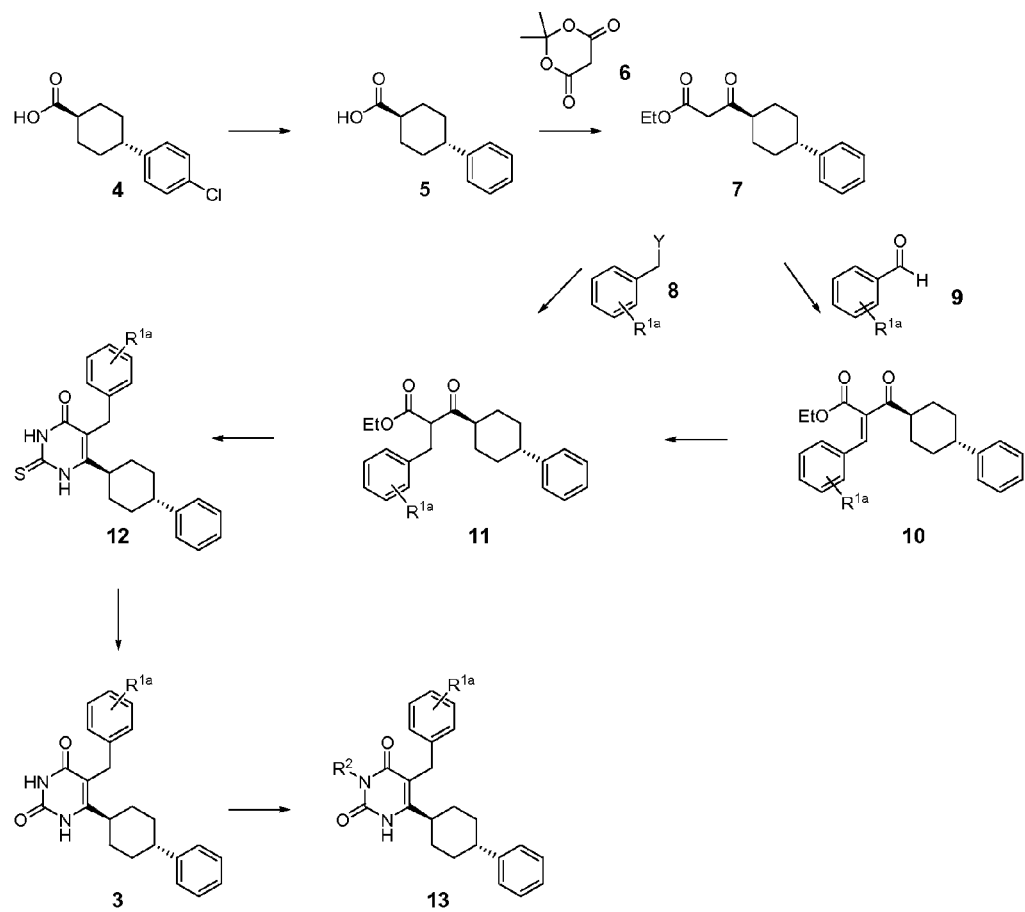
FIG. 2 shows an additional method of making the compounds of the present invention.

Compounds 3 can be prepared by the stereospecific synthesis described in FIG. 2. Commercially available trans-4-(4-chlorophenyl)-cyclohexanecarboxylic acid (4) is hydrogenated in the presence of a palladium on carbon catalyst in an alcohol, preferably ethanol, to afford trans-4-phenyl cyclohexanecarboxylic acid (5). The acid 5 is converted to ketoester 7 by treatment with Meldrum's acid (6) in the presence of 4-dimethylaminopyridine and dicyclohexylcarbodiimide, followed by heating in ethanol. Alkylation of the ketoester 7 can be accomplished by treatment with a base, such as NaH, and a benzyl halide 8 in a solvent such as tetrahydrofuran to afford the benzylated ketoester 11. Alternatively, ketoester 7 can be condensed with a benzaldehyde 9 by heating in toluene in the presence of acetic acid and piperidine to afford the olefin 10. Catalytic hydrogenation of 10 provides the benzylated ketoester 11. Treatment of 11 with thiourea in ethanol in the presence of sodium ethoxide gives the 2-thioxo-2,3-dihydro-1H-pyrimidin-4-ones 12 which are subsequently converted to the subject compounds 3 by acid hydrolysis, preferably with aqueous chloroacetic acid in dioxane.

Compounds in which $R^2$ is a heteroaryl group are similarly prepared by using a heteroaryl methyl halide or a heteroaryl aldehyde in place of the benzyl halide (8) or benzaldehyde (9) in FIG. 2.

Compounds in which $R^1$ are alkyl or substituted alkyl groups can be prepared by treatment of 3 with a base, such as sodium hydride, and the requisite alkylating agent, preferably an alkyl halide or substituted alkyl halide.

IV. Pharmaceutical Compositions

In some embodiments, the present invention provides a pharmaceutical composition including a pharmaceutically acceptable excipient and the compound of formula I.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The GR modulators of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to, sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GR modulators of the invention can be delivered by transdermally, by a topical route, formulated as applicator sticks, solutions, suspensions, emulsions, gels, creams, ointments, pastes, jellies, paints, powders, and aerosols.

The GR modulators and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR modulator pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%0-2% sucrose, 2%-7% mannitol at a pH range of 4.5 to 5.5, that is combined with buffer prior to use In another embodiment, the GR modulator formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of GR modulator formulations can be administered depending on the dosage and frequency as required and tolerated by the patient. The formulations should provide a sufficient quantity of active agent to effectively treat the disease state. Thus, in one embodiment, the pharmaceutical formulations for oral administration of GR modulator is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR modulator formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GR modulator of the invention has been formulated in an acceptable carrier, it can be placed in an appropriate container and labeled for treatment of an indicated condition. For administration of GR modulators, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

V. Method of Treating via Glucocorticoid Modulation

In some embodiments, the present invention provides a method of treating a disorder or condition through modulating a glucocorticoid receptor, the method including administering to a subject in need of such treatment, a therapeutically effective amount of a compound of formula I.

In some other embodiments, the present invention provides a method of treating a disorder or condition through antagonizing a glucocorticoid receptor, the method including administering to a subject in need of such treatment, an effective amount of the compound of formula I.

In another embodiment, the present invention provides methods of modulating glucocorticoid receptor activity using the techniques described herein. In an exemplary embodiment, the method includes contacting a GR with an effective amount of a compound of the present invention, such as the compound of formula I, and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for the NR. In another embodiment, the specific glucocorticoid receptor antagonist binds to the GR with an association constant ($K_d$) that is at least 100-fold less than the $K_d$ for the NR. In another embodiment, the specific glucocorticoid receptor antagonist binds to the GR with an association constant ($K_d$) that is at least 1000-fold less than the $K_d$ for the NR.

Examples of disorders or conditions suitable for use with present invention include, but are not limited to, obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some embodiments, the disorder or condition is major psychotic depression, stress disorders or antipsychotic induced weight gain.

VI. Assays and Methods for Modulating Glucocorticoid Receptor Activity

The compounds of the present invention can be tested for their antiglucocorticoid properties. Methods of assaying compounds capable of modulating glucocorticoid receptor activity are presented herein. Typically, compounds of the current invention are capable of modulating glucocorticoid receptor activity by selectively binding to the GR or by preventing GR ligands from binding to the GR. In some embodiments, the compounds exhibit little or no cytotoxic effect.

A. Binding Assays

In some embodiments, GR modulators are identified by screening for molecules that compete with a ligand of GR, such as dexamethasone. Those of skill in the art will recognize that there are a number of ways to perform competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B. V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

B. Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR. Typically, ligand-binding fragments will comprise transmembrane regions and/or most or all of the extracellular domains of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phospahte (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NFkB or AP-1 transcription factors in transfected cell-lines.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect.

C. Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. GR binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

VII. Examples

LCMS Methods

Method A: experiments were performed using a Waters Platform LC quadrupole mass spectrometer with positive and negative ion electrospray and ELS/Diode array detection using a Phenomenex Luna 3 micron C18 (2) 30×4.6 mm column and a 2 mL/minute flow rate. The solvent system was a 95% water containing 0.1% formic acid (solvent A) and a 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method B: experiments were performed using a Waters Micromass ZQ2000 quadrupole mass spectrometer with a positive and negative ion electrospray and ELS/Diode array detection using a Higgins Clipeus 5 micron C18 100×3.0 mm column and a 1 mL/minute flow rate. The initial solvent system was 95% water containing 0.1% formic acid (solvent A) and a 5% acetonitrile containing 0.1% formic acid (solvent B) for the first minute followed by a gradient up to 5% solvent A and 95% solvent B over the next 8 minutes. The final solvent system was held constant for a further 5 minutes.

Method C: experiments were performed using a Waters ZMD quadrupole mass spectrometer with positive and negative ion electrospray and ELS/Diode array detection using a Phenomenex Luna 3 micron C18 (2) 30×4.6 mm column and a 2 mL/minute flow rate. The solvent system was a 95% water containing 0.1% formic acid (solvent A) and a 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method D: experiments were performed using a Waters Micromass ZQ2000 quadrupole mass spectrometer linked to a Waters Acquity UPLC system with a PDA UV detector using an Acquity UPLC BEH C18 1.7 micron 100×2.1 mm, maintained at 40° C. The spectrometer has an electrospray source operating in positive and negative ion mode. The initial solvent system was 95% water containing 0.1% formic acid (solvent A) and a 5% acetonitrile containing 0.1% formic acid (solvent B) for 0.4 minutes followed by a gradient up to 5% solvent A and 95% solvent B over the next 6.4 minutes.

Method E: experiments were performed using a Waters Quattro Micro triple quadrupole mass spectrometer linked to a Hewlett Packard HP1100 LC system with a positive and negative ion electrospray and ELS/Diode array detection using a Higgins Clipeus 5 micron C18 100×3.0 mm column and a 1 mL/minute flow rate. The initial solvent system was 85% water containing 0.1% formic acid (solvent A) and 15% acetonitrile containing 0.1% formic acid (solvent B) for the first minute followed by a gradient up to 5% solvent A and 95% solvent B over the next 13 minutes. The solvent system was held constant for a further 7 minutes before returning to the initial solvent conditions.

Example 1

Preparation of 5-Benzyl-6-(4-phenylcyclohex-1-enyl)-1H-pyrimidine-2,4-dione (2a)

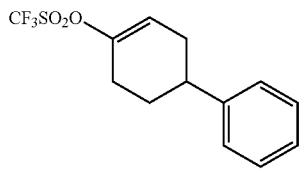

Trifluoromethanesulfonic acid 4-phenyl-cyclohex-1-enyl ester. A solution of diisopropylamine (4.46 mL) in tetrahydrofuran (25 mL) under nitrogen at −20° C. was treated with a 2.5 M solution of n-butyl lithium (12.6 mL) and stirred for 15 minutes. The resulting mixture was cooled to −78° C. before a solution of 4-phenylcyclohexanone (5.0 g) in tetrahydrofuran (20 mL) was added over 20 minutes. The resulting solution was stirred at −78° C. for 3 hours then treated with a solution of N-phenyl-bis(trifluoromethanesulfonimide) (10.76 g) in tetrahydrofuran (25 mL). The mixture was stirred at −78° C. for 1.5 hours then warmed to room temperature and stirred for a further 18 hours. The reaction mixture was concentrated under reduced pressure and the resulting residue partitioned between ethyl acetate and water. The organic layer was washed with 2M sodium hydroxide solution and brine, then dried over sodium sulfate. The solvent was removed under reduced pressure to afford the title compound as an oil (7.3 g). $^1$H NMR (CDCl$_3$): δ 7.32-7.31 (2H, m), 7.24-7.22 (3H, m), 5.87-5.84 (1H, m), 2.85-2.84 (1H, m), 2.55-2.54 (1H, m), 2.44-2.43 (2H, m), 2.35-2.34 (1H, m), 2.09-2.07 (1H, m), 1.96-1.95 (1H, m).

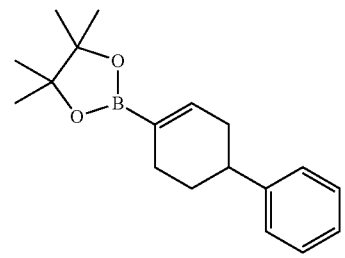 [SMILES: CC1(C)OB(C2=CCC(c3ccccc3)CC2)OC1(C)C]

4,4,5,5-Tetramethyl-2-(4-phenylcyclohex-1-enyl)-[1,3,2]dioxaborolane. A mixture of trifluoro-methanesulfonic acid 4-phenyl-cyclohex-1-enyl ester (5.8 g), bis(pinacolato)diboron (5.3 g), potassium acetate (5.58 g) and [1,1'-bis(diphenylphosphine)ferrocene]dichloropalladium(II) (0.77 g) in 1,4-dioxane (150 mL) was degassed then heated to 80° C. for 2 hours. The reaction mixture was filtered and the resulting filtrate concentrated under reduced pressure. The resulting residue was purified by column chromatography on silica gel, eluting with a mixture of diethyl ether and cyclohexane (0:1 to 1:20 by volume) to afford the title compound (4.0 g). $^1$H NMR (CDCl$_3$): δ 7.30-7.28 (2H, m), 7.24-7.15 (3H, m), 6.65-6.64 (1H, m), 2.82-2.71 (1H, m), 2.40-2.36 (2H, m), 2.23-2.22 (2H, m), 1.95-1.94 (1H, m), 1.70-1.68 (1H, m), 1.43 (3H, s), 1.28 (9H, s).

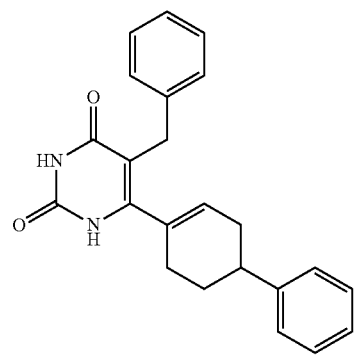 [SMILES: O=c1[nH]c(C2=CCC(c3ccccc3)CC2)c(Cc2ccccc2)c(=O)[nH]1]

5-Benzyl-6-(4-phenylcyclohex-1-enyl)-1H-pyrimidine-2,4-dione (2a). A mixture of 5-benzyl-6-chloro-1H-pyrimidine-2,4-dione (WO006014394) (1.0 g), 4,4,5,5-tetramethyl-2-(4-phenylcyclohex-1-enyl)-[1,3,2]dioxaborolane (1.4 g), bis[di-tert-butyl(4-dimethylaminophenyl)phosphine]dichloropalladium(II) (0.06 g) and cesium fluoride (1.92 g) in 1,4-dioxane (18 mL) and water (2 mL) was heated at 140° C. in a microwave reactor for 20 minutes. The resulting mixture was diluted with saturated aqueous ammonium chloride and filtered to remove the precipitate. The filtrate was extracted with dichloromethane and the combined organic layers washed with water and brine, then dried over sodium sulfate and concentrated under reduced pressure. The resulting residue was purified by column chromatography on silica gel, eluting with a mixture of methanol and dichloromethane (0:1 to 1:20 by volume) to afford the title compound 2a as an off-white solid (0.48 g). LCMS (Method A): $R_t$=3.56 min. $(M+H)^+$ =359. $^1$H NMR (DMSO-D$_6$): δ 11.06 (1H, s), 10.69 (1H, s), 7.23-7.21 (10H, m), 5.84-5.79 (1H, m), 3.61 (2H, s), 3.57 (1H, s), 2.77-2.67 (1H, m), 2.19-2.16 (3H, m), 1.84-1.81 (1H, m), 1.68-1.67 (1H, m).

Examples 2-4

Preparation of 5-Substituted 6-(4-Phenylcyclohex-1-enyl)-1H-pyrimidine-2,4-diones The intermediates shown in Table 1 were prepared following the procedures described in WO06014394, the contents of which are herein incorporated by reference in their entirety.

TABLE 1

| Previously described chloropyrimidinedione intermediates. | | |
|---|---|---|
| Intermediate | Structure | $^1$H NMR/δ |
| 1a | | (DMSO-d$_6$): 12.00 (1 H, s), 11.42 (1 H, s), 7.16-7.14 (1 H, m), 7.08-7.07 (2 H, m), 6.92-6.87 (1 H, m), 3.59 (2 H, s), 2.31 (3 H, s). |
| 1b | | (DMSO-d$_6$): 12.07 (1 H, s), 11.46 (1 H, s), 7.44-7.43 (1 H, m), 7.25-7.24 (2 H, m), 7.11-7.10 (1 H, m), 3.72 (2 H, s). |
| 1c | | (DMSO-d$_6$): 11.95 (1 H, s), 11.38 (1 H, s), 7.14 (1 H, t, J = 7.46 Hz), 7.02-6.95 (3 H, m), 3.61 (2 H, s), 2.26 (3 H, s). |

The examples shown in Table 2 were prepared using similar methods to those described for Example 1, using intermediates 1a-1c in Table 1 in the final cross coupling.

TABLE 2

5-Substituted 6-(4-phenylcyclohex-1-enyl)-1H-pyrimidine-2,4-diones prepared via palladium-catalyzed cross coupling.

| Example | Compound | Structure | $^1$H NMR/δ | LCMS |
|---|---|---|---|---|
| 2 | 2b | 5-(3-Methyl-benzyl)-6-(4-phenyl-cyclohex-1-enyl)-1H-pyrimidine-2,4-dione | (DMSO-d$_6$): 11.06 (1 H, s), 10.68 (1 H, s), 7.26-7.25 (5 H, m), 7.13 (1 H, t, J = 7.78 Hz), 6.94-6.93 (3 H, m), 5.85-5.79 (1 H, m), 3.57 (2 H, s), 2.76-2.65 (1 H, m), 2.37-2.28 (1 H, m), 2.26 (3 H, s), 2.23-2.09 (2 H, m), 2.04-2.00 (1 H, m), 1.87-1.76 (1 H, m), 1.67-1.65 (1 H, m). | (Method B) R$_t$ = 5.13 min (M + H)$^+$ = 373 |
| 3 | 2c | 5-(2-Chloro-benzyl)-6-(4-phenyl-cyclohex-1-enyl)-1H-pyrimidine-2,4-dione | (DMSO-d$_6$): 11.14 (1 H, s), 10.77 (1 H, s), 7.42-7.41 (1 H, m), 7.24-7.22 (7 H, m), 7.10-7.09 (1 H, m), 5.81-5.75 (1 H, m), 3.67 (2 H, s), 2.71-2.59 (1 H, m), 2.15-2.11 (4 H, m), 1.82-1.73 (1 H, m), 1.59-1.58 (1 H, m). | (Method B) R$_t$ = 5.12 min (M + H)$^+$ = 393 |
| 4 | 2d | 5-(2-Methyl-benzyl)-6-(4-phenyl-cyclohex-1-enyl)-1H-pyrimidine-2,4-dione | (DMSO-d$_6$): 11.08 (1 H, s), 10.70 (1 H, s), 7.31-7.23 (2 H, m), 7.20-7.04 (6 H, m), 6.90-6.89 (1 H, m), 5.82-5.76 (1 H, m), 3.53 (2 H, s), 2.69-2.59 (1 H, m), 2.26 (3 H, s), 2.24-1.94 (4 H, m), 1.81-1.70 (1 H, m), 1.58-1.57 (1 H, m). | (Method B) R$_t$ = 5.05 min (M + H)$^+$ = 373 |

Example 5

Preparation of (E)-5-Benzyl-6-(4-phenylcyclohexyl)-1H-pyrimidine-2,4-dione (3a)

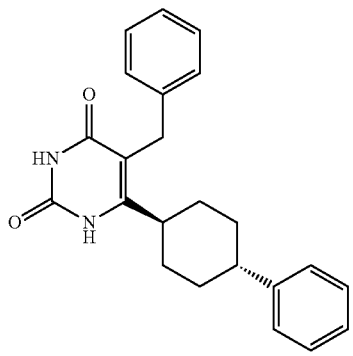 [SMILES: O=c1[nH]c(=O)c(Cc2ccccc2)c([C@H]2CC[C@H](c3ccccc3)CC2)[nH]1]

(E)-5-Benzyl-6-(4-phenylcyclohexyl)-1H-pyrimidine-2,4-dione (3a). A solution of 5-benzyl-6-(4-phenylcyclohex-1-enyl)-1H-pyrimidine-2,4-dione (2a) (380 mg) in a [5:2] mixture of IMS/DCM was hydrogenated over Pd(OH)$_2$ (150 mg) and 10% Pd/C (100 mg) at 45 psi at 50° C. for 18 hours. The crude reaction mixture was degassed with Argon, filtered through a Celite pad and concentrated in vacuuo to give a cream solid. 1H NMR showed a mixture of cis/trans isomers, a portion of which was separated into individual isomers using a C18 Synergy column eluting with 70-80% MeOH/water (+0.1% formic acid) over 20 minutes, then isocratic (80%) for a further 5 minutes. $^1$H NMR (cyclohexane bridgehead protons coupling constants) allowed assignment of the first eluting isomer as the trans isomer 3a and the second as the cis isomer 3bb. First-eluting isomer 3a: $R_t$=10.86 min, (M+H)$^+$=361. Second-eluting cis isomer 3bb: $R_t$=11.01 min, (M+H)$^+$=361.

Example 6

Preparation of (E)-6-(4-Phenylcyclohexyl)-5-(3-trifluoromethylbenzyl)-1H-pyrimidine-2,4-dione (3b)

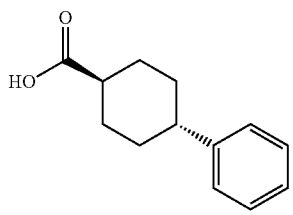 [SMILES: O=C(O)[C@H]1CC[C@H](c2ccccc2)CC1]

(E)-4-Phenylcyclohexanecarboxylic acid (5). A mixture of (E)-4-(4-chlorophenyl)-cyclohexanecarboxylic acid (4) (15 g) and 10% palladium on carbon (4 g) in ethanol (400 mL) was stirred under an atmosphere of hydrogen for 4 days. The reaction mixture was diluted with dichloromethane, filtered through Celite® and the filtrate concentrated under reduced pressure. The resulting residue was dissolved in ethanol (150 mL) and treated with 5 M aqueous sodium hydroxide (25 mL). The resulting mixture was stirred at room temperature for 16 hours then concentrated under reduced pressure. The residue was treated with 1 M aqueous hydrochloric acid (200 mL) and stirred for 15 minutes then extracted with ethyl acetate. The combined organic phases were dried over sodium sulfate and concentrated under reduced pressure to afford the title compound as a white solid (11 g). $^1$H NMR (CDCl$_3$): δ 7.27-7.25 (5H, m), 2.52 (1H, tt, J=11.90, 3.44 Hz), 2.48-2.29 (1H, m), 2.17-2.14 (2H, m), 2.02-1.98 (2H, m), 1.56-1.55 (4H, m).

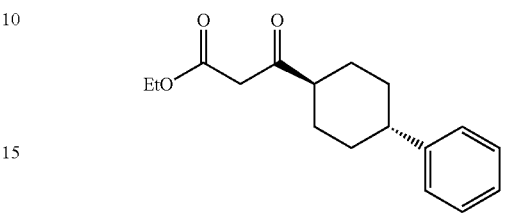

(E)-3-Oxo-3-(4-phenylcyclohexyl)-propionic acid ethyl ester (7). A mixture of (E)-4-phenylcyclohexanecarboxylic acid (5) (11 g), dimethylpyridin-4-yl-amine (7.3 g), 2,2-dimethyl-[1,3]dioxane-4,6-dione (8.5 g) and 4 Å molecular sieves (2.0 g) in dichloromethane (200 mL) was stirred at room temperature for 10 minutes then treated with a solution of dicyclohexylcarbodiimide (12.4 g) in dichloromethane (40 mL). The resulting mixture was stirred at room temperature for 1.5 hours then filtered and the filtrate washed with 1 M aqueous hydrochloric acid and water, then dried over sodium sulfate and concentrated under reduced pressure. The resulting solid was dissolved in ethanol (100 mL) and heated at reflux for 1.5 hours then concentrated under reduced pressure. The resulting residue was purified by column chromatography on silica gel, eluting with a mixture of ethyl acetate and cyclohexane (0:1 to 3:7 by volume) to afford the title compound as a white solid (11 g). $^1$H NMR (CDCl$_3$): δ 7.23-7.22 (5H, m), 4.25-4.17 (2H, m), 3.52 (2H, s), 2.54-2.53 (2H, m), 2.09-1.99 (4H, m), 1.54-1.51 (4H, m), 1.32-1.25 (3H, m).

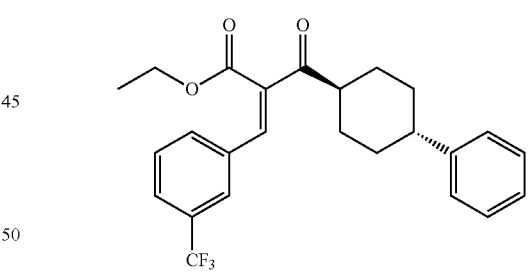

(Z)-2-(4-Phenylcyclohexanecarbonyl)-3-(3-trifluoromethylphenyl)-acrylic acid ethyl ester (10). 3-Oxo-3-(4-phenyl-cyclohexyl)-propionic acid ethyl ester (7) (11.56 g, 42.1 mmol), 3-trifluoromethylbenzaldehyde (11 g, 63.15 mmol), glacial acetic acid (7.16 mmol, 0.41 mL) and piperidine (2.1 mmol, 0.21 mL) were dissolved in toluene (250 mL) and heated under Dean and Stark conditions at reflux for 48 hours. The cooled reaction mixture was diluted with an equal volume of ethyl acetate and washed with 1M aq. HCl and brine. The organics were dried over sodium sulfate, filtered, and evaporated to afford a clear, brown oil. The residue was purified by column chromatography on silica gel (gradient: 0 to 10% tert-butyl methyl ether in cyclohexane) to afford 12.3 g (68%) of (Z)-2-(4-phenylcyclohexanecarbonyl)-3-(3-trifluoromethyl-phenyl)-acrylic acid ethyl ester. ¹H NMR (400 MHz, 192191), LCMS (method C), R_t=4.77 min, (M+H)⁺=431.2.

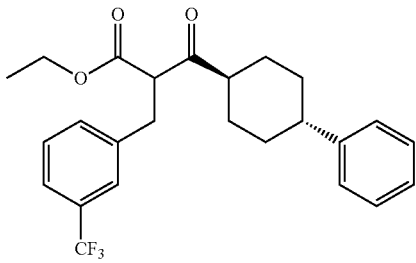 [SMILES: CCOC(=O)C(Cc1cccc(C(F)(F)F)c1)C(=O)[C@H]1CC[C@H](c2ccccc2)CC1]

3-Oxo-3-(4-phenylcyclohexyl)-2-(3-trifluoromethylbenzyl)-propionic acid ethyl ester (11). A mixture of (Z)-2-(4-phenylcyclohexanecarbonyl)-3-(3-trifluoromethylphenyl)-acrylic acid ethyl ester (10) (12.3 g, 28.6 mmol) and 100/Pd on carbon (2.5 g, 20% by weight) in denatured ethanol (250 mL) was stirred under a hydrogen atmosphere for 2 hr. The solids were removed by filtration through celite and washed with ethanol. The filtrate was evaporated under vacuum to yield a clear oil. The residue was purified by column chromatography on silica gel (gradient: 0 to 10% tert-butyl methyl ether in cyclohexane) to afford 8.6 g (70%) of 3-oxo-3-(4-phenylcyclohexyl)-2-(3-trifluoromethylbenzyl)-propionic acid ethyl ester (22). ¹H NMR (400 MHz, 192227). LCMS (method A), R_t=4.76 min, (M+H)⁺=433.2 (94%); R=5.22 min, (M+H)+=262.9 (6.5%).

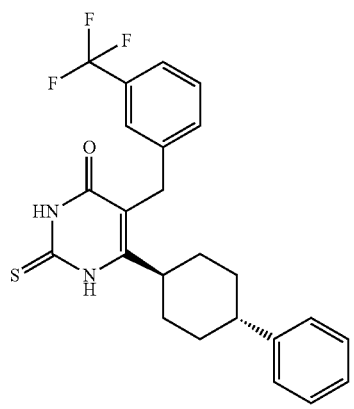 [SMILES: O=c1[nH]c(=S)[nH]c([C@H]2CC[C@H](c3ccccc3)CC2)c1Cc1cccc(C(F)(F)F)c1]

(E)-6-(4-Phenylcyclohexyl)-2-thioxo-5-(3-trifluoromethylbenzyl)-2,3-dihydro-1H-pyrimidin-4-one (12a). Sodium (5 g, 217.8 mmol) and thiourea (18 g, 236 mmol) were dissolved in absolute ethanol (300 mL) and heated at reflux under nitrogen for 1 hr. The reaction mixture was cooled to 0° C. and 3-oxo-3-(4-phenylcyclohexyl)-2-(3-trifluoromethylbenzyl)-propionic acid ethyl ester (11) (15.7 g, 36.3 mmol) in absolute ethanol (150 mL) was added slowly (reaction mixture temperature <10° C.). The reaction mixture was heated at reflux for 1.5 hr. The reaction mixture was cooled then evaporated under vacuum to a peach-colored solid. The solid was suspended in water (500 mL) and adjusted to pH=5 with glacial acetic acid. The resulting precipitate was isolated by filtration, re-dissolved in DCM, and passed through a phase separation cartridge to remove water. The filtrate was evaporated to an off-white solid that was triturated in hot methanol. The solid was recovered by filtration and dried under vacuum at 50° C. to afford 4.8 g (30%) of the title compound. ¹H NMR (400 MHz, 192268). LCMS (method C): R_t=4.10 min, (M+H)⁺=444.9.

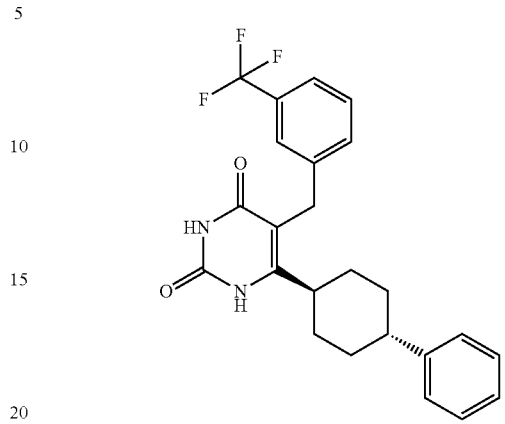

(E)-6-(4-Phenylcyclohexyl)-5-(3-trifluoromethylbenzyl)-1H-pyrimidine-2,4-dione (3b). (E)-6-(4-Phenylcyclohexyl)-2-thioxo-5-(3-trifluoromethylbenzyl)-2,3-dihydro-1H-pyrimidine-4-one (12a) (4.8 g, 10.8 mmol) was suspended in dioxane (150 mL), and 10%0/(w/v) aqueous chloroacetic acid (100 mL) was added. The reaction mixture was heated at 100° C., and further dioxane (25 mL) was added to effect complete dissolution. Heating was continued for 64 hr. The cooled reaction mixture was diluted with water and extracted with dichloromethane. The combined organics were washed with saturated aqueous sodium carbonate and brine, dried over sodium sulfate, filtered, and evaporated to yield an off-white solid that was triturated in hot methanol. The solid was recovered by filtration and dried under vacuum at 50° C. to afford 3.7 g (80%) of the title compound. ¹H NMR (DMSO-d₆): δ 11.12 (1H, s), 10.52 (1H, s), 7.61 (1H, s), 7.51 (3H, m), 7.30-7.13 (5H, m), 3.83 (2H, s), 2.90 (1H, m), 1.83-1.80 (4H, m), 1.50-1.40 (4H, m). LCMS (method B): R_t=5.26 min, (M+H)⁺=429.01.

Example 7

Preparation of (E)-5-(3-Methylbenzyl)-6-(4-phenylcyclohexyl)-1H-pyrimidine-2,4-dione (3 h)

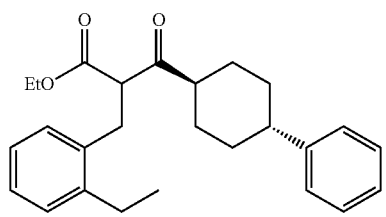 [SMILES: CCOC(=O)C(Cc1ccccc1CC)C(=O)[C@H]1CC[C@H](c2ccccc2)CC1]

(E)-2-(2-Ethylbenzyl)-3-oxo-3-(4-phenylcyclohexyl)-propionic acid ethyl ester (11a). A suspension of sodium hydride (0.07 g) in tetrahydrofuran (10 mL) was treated with a solution of (E)-3-oxo-3-(4-phenylcyclohexyl)-propionic acid ethyl ester (7) (0.50 g) in tetrahydrofuran (8 mL), and the resulting mixture stirred for 1 hour at room temperature. 1-Bromomethyl-2-ethylbenzene (0.38 g) was added and the resulting mixture was refluxed for 2 hours, cooled to room temperature, and quenched by addition of 1 M aqueous hydrochloric acid. The aqueous phase was extracted with ethyl acetate and the combined organic phases were washed with brine, dried over magnesium sulfate, and concentrated under reduced pressure. The resulting residue was purified by column chromatography on silica gel eluting with a mixture of dichloromethane and cyclohexane (0:1 to 4:6 by volume) to afford the title compound (0.86 g). $^1$H NMR (CDCl$_3$): δ 7.31-7.27 (1H, m), 7.17-7.16 (6H, m), 7.09-7.08 (2H, m), 4.16-4.16 (2H, m), 3.97 (1H, t, J=7.47 Hz), 3.22-3.21 (2H, m), 2.68 (2H, q, J=7.55 Hz), 2.41-2.41 (2H, m), 1.94-1.92 (3H, m), 1.75-1.68 (1H, m), 1.54 (1H, s), 1.40-1.39 (3H, m), 1.27-1.18 (6H, m).

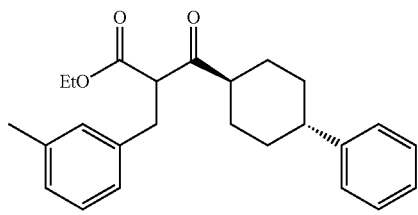 [SMILES: CCOC(=O)C(Cc1cccc(C)c1)C(=O)[C@H]1CC[C@H](c2ccccc2)CC1]

(E)-2-(3-Methylbenzyl)-3-oxo-3-(4-phenylcyclohexyl)-propionic acid ethyl ester (11 h). The title compound was prepared as described for compound 11a above. $^1$H NMR (CDCl$_3$): 7.29 (2H, m), 7.17-7.12 (4H, m), 7.02-6.95 (3H, m), 4.16 (2H, qd, J=7.13, 2.38 Hz), 3.95 (1H, t, J=7.51 Hz), 3.13 (2H, dd, J=7.52, 2.32 Hz), 2.45 (2H, m), 2.31 (3H, s), 1.97-1.94 (3H, m), 1.80-1.73 (1H, m), 1.53-1.27 (4H, m), 1.22 (3H, t, J=7.13 Hz).

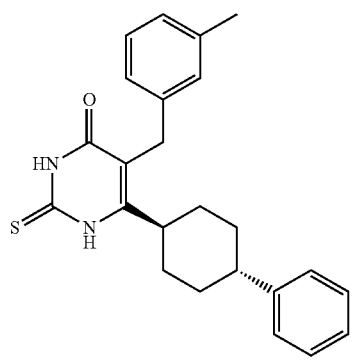 [SMILES: Cc1cccc(Cc2c(=O)[nH]c(=S)[nH]c2[C@H]2CC[C@H](c3ccccc3)CC2)c1]

(E)-6-(4-Phenylcyclohexyl)-2-thioxo-5-(3-methylbenzyl)-2,3-dihydro-1H-pyrimidin-4-one (12 g). The title compound was prepared from compound 11 h as described for compound 12a above. LCMS (method A): R$_t$=4.07 min, (M+H)$^+$=391.

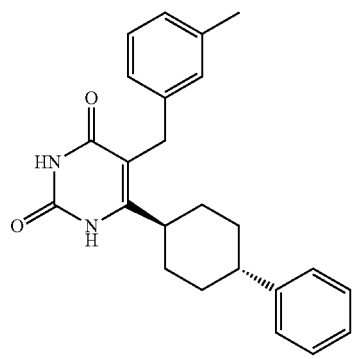 [SMILES: Cc1cccc(Cc2c(=O)[nH]c(=O)[nH]c2[C@H]2CC[C@H](c3ccccc3)CC2)c1]

(E)-5-(3-Methylbenzyl)-6-(4-phenylcyclohexyl)-1H-pyrimidine-2,4-dione (3 h). The title compound was prepared from compound 12 g as described for compound 3b above. $^1$H NMR (DMSO-d6): 11.06 (1H, s), 10.46 (1H, s), 7.32-7.24 (2H, m), 7.18-7.16 (4H, m), 7.00-6.98 (3H, m), 3.68 (2H, s), 2.90-2.79 (1H, m), 2.48-2.44 (1H, m), 2.25 (3H, s), 1.91-1.73 (4H, m), 1.46-1.43 (4H, m). LCMS (method B), R$_t$=5.17 min, (M+H)$^+$=375.

Examples 8-34

Preparation of 5-Substituted (E)-6-(4-cyclohexyl-1H-pyrimidine-2,4-diones

Intermediates 11 in Table 3 below were prepared from 7b as described for compound 11a in Example 7.

TABLE 3

2-Substituted (E)-3-oxo-3-(4-phenylcyclohexyl)-propionic acid ethyl esters.

| Intermediate | Structure | $^1$H NMR/δ |
|---|---|---|
| 11b | (structure) | (CDCl$_3$): 7.30-7.15 (10 H. m), 4.16 (2 H, qd, J = 7.12, 2.88 Hz), 3.96 (1 H, t, J = 7.55 Hz), 3.18-3.16 (2 H, m), 2.44 (2 H, td, J = 11.85, 3.23 Hz), 1.93-1.90 (3 H, m), 1.74-1.73 (1 H, m), 1.51-1.49 (2 H, m), 1.37-1.36 (2 H, m), 1.22 (3 H, t, J = 7.13 Hz). |

TABLE 3-continued

2-Substituted (E)-3-oxo-3-(4-phenylcyclohexyl)-propionic acid ethyl esters.

| Intermediate | Structure | $^1$H NMR/δ |
|---|---|---|
| 11c | 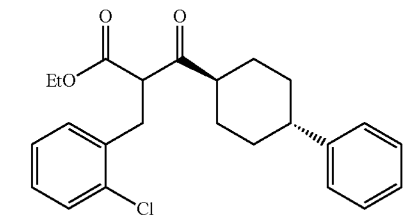 [SMILES: CCOC(=O)C(Cc1ccccc1Cl)C(=O)[C@H]1CC[C@H](c2ccccc2)CC1] | (CDCl$_3$): 7.35-7.17 (9 H, m), 4.20-4.13 (3 H, m), 3.28 (2 H, m), 2.48-2.47 (2 H, m), 1.95-1.92 (3 H, m), 1.77-1.75 (1 H, m), 1.55-1.35 (3 H, m), 1.23-1.15 (1 H, m), 1.22 (3 H, t, J = 7.14 Hz). |
| 11d | 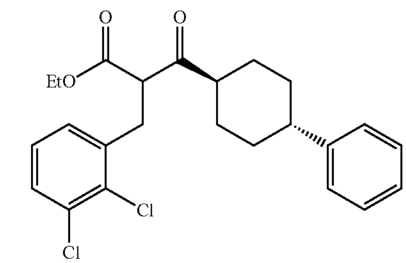 [SMILES: CCOC(=O)C(Cc1cccc(Cl)c1Cl)C(=O)[C@H]1CC[C@H](c2ccccc2)CC1] | (CDCl$_3$): 7.37-7.26 (3 H, m), 7.22-7.07 (5 H, m), 4.17-4.16 (3 H, m), 3.32 (2 H, d, J = 7.39 Hz), 2.58-2.41 (2 H, m), 1.97-1.95 (3 H, m), 1.81-1.80 (1 H, m), 1.44 (3 H, m), 1.30-1.18 (1 H, m), 1.24 (3 H, t, J = 7.14 Hz). |
| 11e | 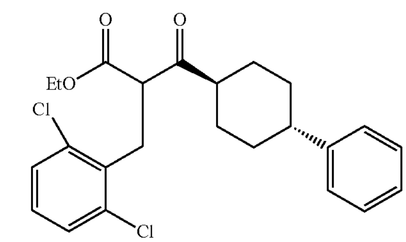 [SMILES: CCOC(=O)C(Cc1c(Cl)cccc1Cl)C(=O)[C@H]1CC[C@H](c2ccccc2)CC1] | (CDCl$_3$): 7.29 (4 H, m), 7.21-7.09 (4 H, m), 4.19-4.09 (3 H, m), 3.59-3.45 (2 H, m), 2.53-2.43 (2 H, m), 1.97-1.94 (4 H, m), 1.61-1.60 (2 H, m), 1.48-1.45 (1 H, m), 1.39-1.38 (1 H, m), 1.21 (3 H, t, J = 7.15 Hz). |
| 11f | 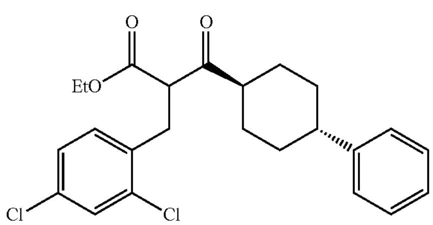 [SMILES: CCOC(=O)C(Cc1ccc(Cl)cc1Cl)C(=O)[C@H]1CC[C@H](c2ccccc2)CC1] | (CDCl$_3$): 7.37 (1 H, d, J = 2.04 Hz), 7.31-7.25 (2 H, m), 7.20-7.14 (5 H, m), 4.15-4.14 (3 H, m), 3.24 (2 H, d, J = 7.44 Hz), |
| 11g | 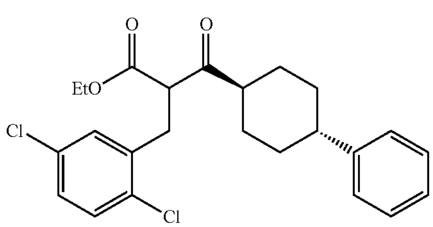 [SMILES: CCOC(=O)C(Cc1cc(Cl)ccc1Cl)C(=O)[C@H]1CC[C@H](c2ccccc2)CC1] | (CDCl$_3$): 7.31-7.14 (8 H, m), 4.16-4.15 (3 H, m), 3.24 (2 H, d, J = 7.43 Hz), 2.60-2.43 (2 H, m), 2.02-1.90 (3 H m), 1.87-1.80 (1 H, m), 1.64-1.39 (3 H, m), 1.34-1.24 (1 H, m), 1.24 (3 H, t, J = 7.13 Hz). |
| 11i | 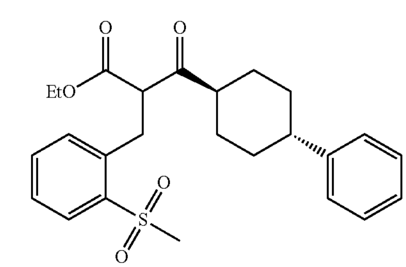 [SMILES: CCOC(=O)C(Cc1ccccc1S(C)(=O)=O)C(=O)[C@H]1CC[C@H](c2ccccc2)CC1] | (CDCl$_3$): 8.05 (1 H, dd, J = 7.91, 1.50 Hz), 7.53 (1 H, td, J = 7.52, 1.53 Hz), 7.44 (1 H, td, J = 7.68, 1.47 Hz), 7.35 (1 H, d, J = 7.65 Hz), 7.29 (2 H, m), 7.16-7.15 (3 H, m), 4.39 (1 H, t, J = 7.20 Hz), 4.21-4.09 (2 H, m), 3.56-3.42 (2 H, m), 3.11 (3 H, s), 2.59-2.49 (1 H, m), 2.48-2.39 (1 H, m), 1.98-1.86 (3 H, m), 1.84-1.76 (1 H, m), 1.60-1.33 (3 H, m), 1.22-1.15 (1 H, m), 1.21 (3 H, t, J = 7.13 Hz). |

TABLE 3-continued

2-Substituted (E)-3-oxo-3-(4-phenylcyclohexyl)-propionic acid ethyl esters.

| Intermediate | Structure | ¹H NMR/δ |
|---|---|---|
| 11j | 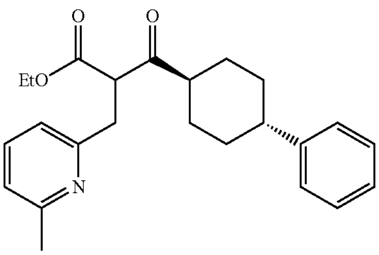 [SMILES: CCOC(=O)C(Cc1cccc(C)n1)C(=O)[C@H]1CC[C@H](c2ccccc2)CC1] | (CDCl$_3$): 7.45 (1 H, s), 7.32-7.24 (2 H, m), 7.21-7.15 (3 H, m), 6.96 (2 H, m), 4.47 (1 H, s), 4.17-4.16 (2 H, m), 3.33 (2 H, m), 2.69 (1 H, m), 2.49 (3 H, s), 1.97 (4 H, m), 1.50-1.48 (2 H, m), 1.30 (1 H, m), 1.24 (3 H, t, J = 7.13 Hz). |
| 11k | 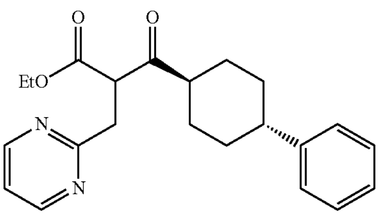 [SMILES: CCOC(=O)C(Cc1ncccn1)C(=O)[C@H]1CC[C@H](c2ccccc2)CC1] | (CDCl$_3$): 8.65 (1 H, s), 8.64 (1 H, s), 7.33-7.28 (2 H, m), 7.22-7.17 (3 H, m), 7.13 (1 H, t, J = 4.95 Hz), 4.55 (1 H, m), 4.25-4.18 (2 H, m), 3.70-3.50 (2 H, m), 2.80 (1 H, m), 2.53 (1 H, m), 2.17 (1 H, m), 2.09-1.97 (3 H, m), 1.69-1.42 (4 H, m), 1.27 (3 H, t, J = 7.12 Hz). |
| 11l | 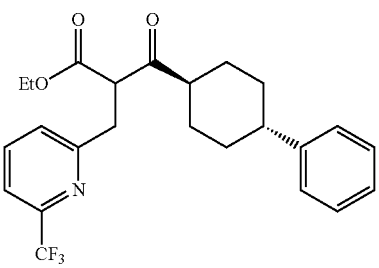 [SMILES: CCOC(=O)C(Cc1cccc(C(F)(F)F)n1)C(=O)[C@H]1CC[C@H](c2ccccc2)CC1] | (CDCl$_3$): 7.76 (1 H, td, J = 7.80, 0.78 Hz), 7.51 (1 H, d, J = 7.71 Hz), 7.41 (1 H, d, J = 7.88 Hz), 7.33-7.26 (2 H, m), 7.22-7.17 (3 H, m), 4.61 (1 H, dd, J = 8.73, 5.96 Hz), 4.21 (2 H, qd, J = 7.14, 1.24 Hz), 3.56-3.35 (2 H, m), 2.78-2.77 (1 H, m), 2.48-2.47 (1 H, m), 2.01 (4 H, m), 1.51-1.50 (3 H, m), 1.35-1.26 (1 H, m), 1.28 (3 H, t, J = 7.14 Hz). |
| 11m | 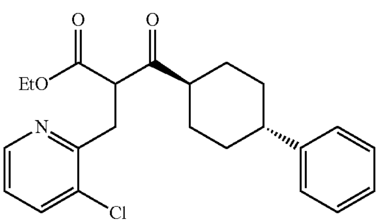 [SMILES: CCOC(=O)C(Cc1ncccc1Cl)C(=O)[C@H]1CC[C@H](c2ccccc2)CC1] | (CDCl$_3$): 8.34 (1 H, dd, J = 4.65, 1.63 Hz), 7.64 (1 H, dd, J = 8.01, 1.56 Hz), 7.31 (2 H, m), 7.25-7.18 (3 H, m), 7.10 (1 H, dd, J = 7.98, 4.74 Hz), 4.58 (1 H, dd, J = 8.13, 6.40 Hz), 4.22 (2 H, q, J = 7.13 Hz), 3.62-3.39 (2 H, m), 2.81 (1 H, m), 2.53 (1 H, m), 2.20-1.95 (4 H, m), 1.68-1.41 (4 H, m), 1.28 (3 H, t, J = 7.12 Hz). |
| 11n | 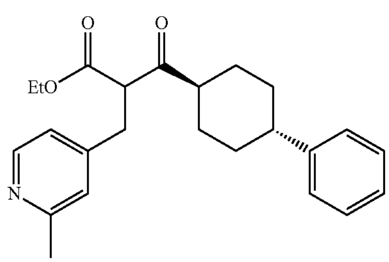 [SMILES: CCOC(=O)C(Cc1ccnc(C)c1)C(=O)[C@H]1CC[C@H](c2ccccc2)CC1] | (CDCl$_3$): 8.40 (1 H, d, J = 5.17 Hz), 7.31 (2 H, m), 7.19 (3 H, m), 7.02 (1 H, s), 6.96 (1 H, d, J = 5.17 Hz), 4.18 (2 H, m), 3.96 (1 H, t, J = 7.46 Hz), 3.14 (2 H, m), 2.54 (3 H, s), 2.60-2.45 (2H, m), 1.97 (2 H, m), 1.86-1.80 (1 H, m), 1.64-1.40 (2 H, m), 1.34-1.28 (1H, m), 1.25 (3 H, t, J = 7.18 Hz). |
| 11o | 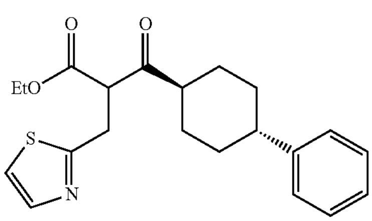 [SMILES: CCOC(=O)C(Cc1nccs1)C(=O)[C@H]1CC[C@H](c2ccccc2)CC1] | (CDCl$_3$): 7.67 (1 H, d, J = 3.33 Hz), 7.30-7.29 (2 H, m), 7.22-7.18 (4 H, m), 4.45 (1 H, m), 4.22 (2 H, qd, J = 7.13, 3.54 Hz), 3.65-3.50 (2 H, m), 2.71 (1 H, m), 2.51-2.50 (1 H, m), 2.06-1.95 (4 H, m), 1.50-1.31 (4 H, m), 1.27 (3 H, t, J = 7.12 Hz). |

TABLE 3-continued

2-Substituted (E)-3-oxo-3-(4-phenylcyclohexyl)-propionic acid ethyl esters.

| Intermediate | Structure | $^1$H NMR/δ |
|---|---|---|
| 11p | 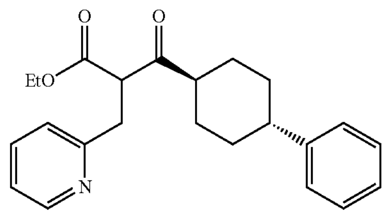 | (CDCl$_3$): 8.51 (1 H, d, J = 4.76 Hz), 7.59 (1 H, t, J = 7.45 Hz), 7.32-7.30 (2 H, m), 7.25-7.08 (5 H, m), 4.51 (1 H, t, J = 7.50 Hz), 4.18 (2 H, m), 3.45-3.28 (2 H, m), 2.69 (1 H, m), 2.48 (1 H, m), 2.07-1.87 (4 H, m), 1.64-1.28 (4 H, m), 1.23 (3 H, t, J = 7.15 Hz). |
| 11q | 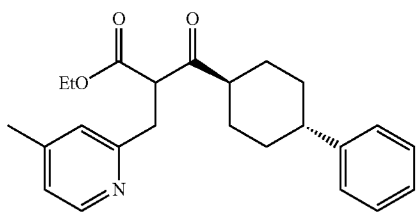 | (CDCl$_3$): 8.34 (1 H, d, J = 5.09 Hz), 7.32-7.26 (2 H, m), 7.22-7.14 (3 H, m), 7.02 (1 H, s), 6.93 (1 H, d, J = 5.25 Hz), 4.49 (1 H, t, J = 7.40 Hz), 4.17 (2 H, qd, J = 7.13, 1.64 Hz), 3.28-3.27 (2 H, m), 2.71-2.64 (1 H, m), 2.52-2.41 (1 H, m), 2.31 (3 H, s), 2.07-1.88 (4 H, m), 1.62-1.30 (4 H, m), 1.23 (3 H, t, J = 7.13 Hz). |
| 11r | 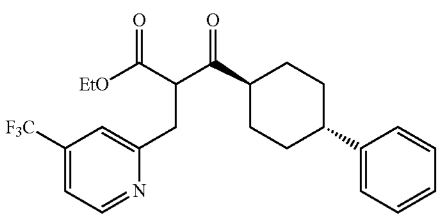 [SMILES: CCOC(=O)C(Cc1cc(C(F)(F)F)ccn1)C(=O)[C@H]1CC[C@H](c2ccccc2)CC1] | (CDCl$_3$): 8.66 (1 H, d, J = 5.07 Hz), 7.43 (1 H, s), 7.36-7.26 (3 H, m), 7.20-7.14 (3 H, m), 4.51 (1 H, m), 4.19 (2 H, qd, J = 7.12, 2.51 Hz), 3.44-3.43 (2 H, m), 2.73-2.72 (1 H, m), 2.50-2.48 (1 H, m), 2.01 (4 H, m), 1.66-1.32 (4 H, m), 1.25 (2 H, t, J = 7.13 Hz). |
| 11s | 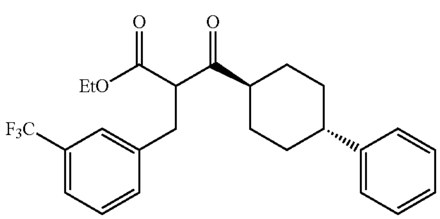 [SMILES: CCOC(=O)C(Cc1cccc(C(F)(F)F)c1)C(=O)[C@H]1CC[C@H](c2ccccc2)CC1] | (CDCl$_3$): 7.47 (2 H, m), 7.41 (2 H, m), 7.29 (2 H, m), 7.19 (3 H, m), 4.18 (2 H, m), 3.98 (1 H, t, J = 7.53 Hz), 3.25 (2 H, m), 2.56-2.41 (2 H, m), 1.96 (3 H, m), 1.79 (1 H, m), 1.61-1.36 (3 H, m), 1.32-1.25 (1 H, m), 1.23 (4 H, t, J = 7.16 Hz). |
| 11t | 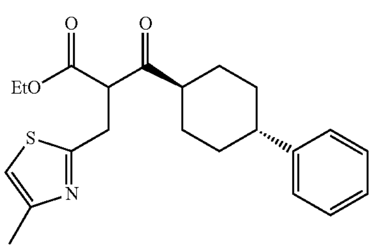 [SMILES: CCOC(=O)C(Cc1nc(C)cs1)C(=O)[C@H]1CC[C@H](c2ccccc2)CC1] | (CDCl$_3$): 7.35-7.28 (2 H, m), 7.20-7.19 (3 H, m), 6.73 (1 H, d, J = 1.15 Hz), 4.39 (1 H, m), 4.20 (2 H, m), 3.60-3.43 (2 H, m), 2.78-2.66 (1 H, m), 2.56-2.45 (1 H, m), 2.39 (3 H, d, J = 1.01 Hz), 2.06-1.95 (4 H, m), 1.53-1.34 (4 H, m), 1.27 (3 H, t, J = 7.14 Hz). |
| 11u | 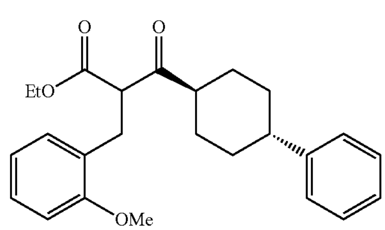 [SMILES: CCOC(=O)C(Cc1ccccc1OC)C(=O)[C@H]1CC[C@H](c2ccccc2)CC1] | (CDCl$_3$): 7.31-7.26 (2 H, m), 7.23-7.09 (5 H, m), 6.88-6.81 (2 H, m), 4.18-4.09 (3 H, m), 3.85 (3 H, s), 3.15 (2 H, d, J = 7.39 Hz), 2.52-2.40 (2 H, m), 2.01-1.87 (3 H, m), 1.84-1.73 (1 H, m), 1.57-1.28 (4 H, m), 1.20 (3 H, t, J = 7.13 Hz). |

TABLE 3-continued

2-Substituted (E)-3-oxo-3-(4-phenylcyclohexyl)-propionic acid ethyl esters.

| Intermediate | Structure | $^1$H NMR/δ |
|---|---|---|
| 11v | 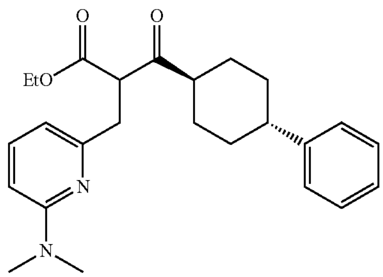 [SMILES: CCOC(=O)C(Cc1cccc(N(C)C)n1)C(=O)[C@H]1CC[C@H](c2ccccc2)CC1] | (CDCl$_3$): 7.30-7.29 (3 H, m), 7.21-7.15 (3 H, m), 6.42 (1 H, d, J = 7.19 Hz), 6.31 (1 H, d, J = 8.43 Hz), 4.48 (1 H, t, J = 7.21 Hz), 4.23-4.10 (2 H, m), 3.29-3.12 (2 H, m), 3.04 (6 H, s), 2.65 (1 H, m), 2.47 (1 H, m), 2.05-1.91 (4 H, m), 1.54-1.35 (4 H, s), 1.23 (2 H, t, J = 7.13 Hz). |
| 11w | 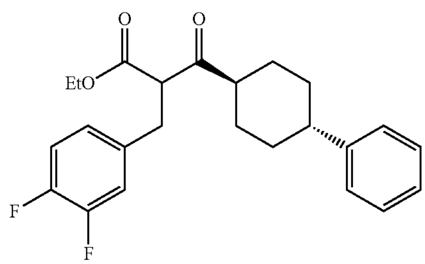 [SMILES: CCOC(=O)C(Cc1ccc(F)c(F)c1)C(=O)[C@H]1CC[C@H](c2ccccc2)CC1] | (CDCl$_3$): 7.33-6.70 (8 H, m), 4.17-4.16 (2 H, m), 3.89 (1 H, m), 3.13 (2 H, m), 2.49 (2 H, m), 2.01-1.85 (3 H, m), 1.78 (1 H, m), 1.67-1.29 (4 H, m), 1.23 (3 H, t, J = 6.99 Hz). |
| 11x | 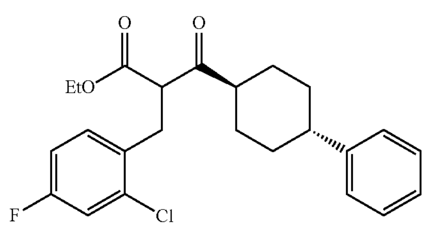 [SMILES: CCOC(=O)C(Cc1ccc(F)cc1Cl)C(=O)[C@H]1CC[C@H](c2ccccc2)CC1] | (CDCl$_3$): 7.31-7.26 (2 H, m), 7.23-7.15 (4 H, m), 7.12-7.08 (1 H, dd, J = 8.41, 2.65 Hz), 6.89 (1 H, td, J = 8.30, 2.65 Hz), 4.22-4.09 (3 H, m), 3.24 (2 H, d, J = 7.47 Hz), 2.57-2.40 (2 H, m), 2.00-1.89 (3 H, m), 1.82-1.74 (1 H, m), 1.60-1.54 (1 H, m), 1.51-1.37 (2 H, m), 1.26-1.18 (1 H, m), 1.23 (3 H, t, J = 7.13 Hz). |
| 11y | 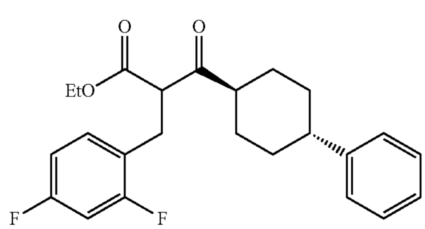 [SMILES: CCOC(=O)C(Cc1ccc(F)cc1F)C(=O)[C@H]1CC[C@H](c2ccccc2)CC1] | (CDCl$_3$): 7.31-7.26 (2 H, m), 7.20-7.15 (4 H, m), 6.80-6.77 (2 H, m), 4.22-4.08 (2 H, m), 4.02 (1 H, t, J = 7.56 Hz), 3.16 (2 H, d, J = 7.61 Hz), 2.60-2.41 (2 H, m), 1.97-1.91 (3 H, m), 1.86-1.77 (1 H, m), 1.61-1.39 (2 H, m), 1.23 (3 H, t, J = 7.14 Hz). |

Intermediates 11 were converted to Intermediates 12 in Table 4 below, as described for the preparation of 12a in Example 6.

TABLE 4

Substituted 2-thioxo-2,3-dihydro-pyrimidine-4-ones.

| Compound | Structure | LCMS |
| --- | --- | --- |
| 12b | 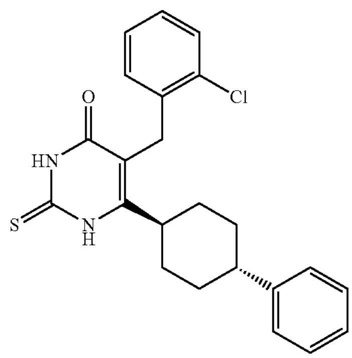 [SMILES: O=c1[nH]c(=S)[nH]c([C@H]2CC[C@H](c3ccccc3)CC2)c1Cc1ccccc1Cl] | (Method A)<br>$R_t$ = 4.10 min<br>$(M + H)^+$ = 411 |
| 12c | 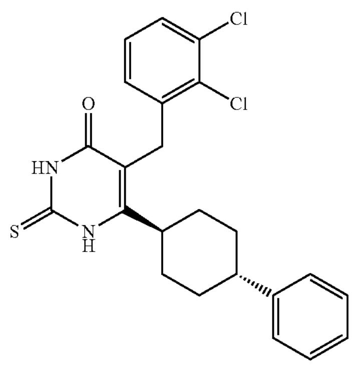 [SMILES: O=c1[nH]c(=S)[nH]c([C@H]2CC[C@H](c3ccccc3)CC2)c1Cc1cccc(Cl)c1Cl] | (Method A)<br>$R_t$ = 4.27 min<br>$(M + H)^+$ = 445 |
| 12d | 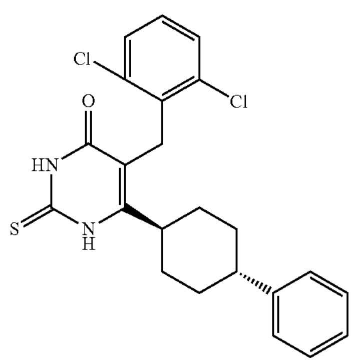 [SMILES: O=c1[nH]c(=S)[nH]c([C@H]2CC[C@H](c3ccccc3)CC2)c1Cc1c(Cl)cccc1Cl] | (Method C)<br>$R_t$ = 4.16 min<br>$(M + H)^+$ = 445 |
| 12e | 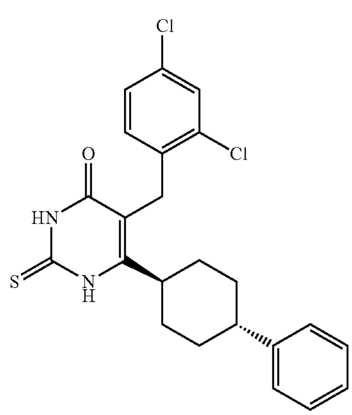 [SMILES: O=c1[nH]c(=S)[nH]c([C@H]2CC[C@H](c3ccccc3)CC2)c1Cc1ccc(Cl)cc1Cl] | (Method A)<br>$R_t$ = 4.35 min<br>$(M + H)^+$ = 445 |

TABLE 4-continued
Substituted 2-thioxo-2,3-dihydro-pyrimidine-4-ones.
| Compound | Structure | LCMS |
|---|---|---|
| 12f | 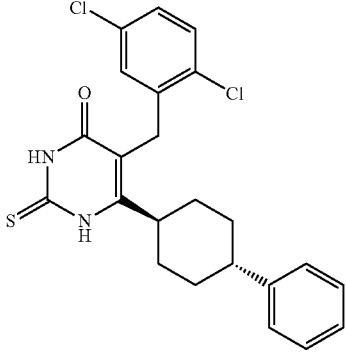 [SMILES: O=c1[nH]c(=S)[nH]c([C@H]2CC[C@H](c3ccccc3)CC2)c1Cc1cc(Cl)ccc1Cl] | No LCMS or NMR data available (MXS2705-154-04). |
| 12h | 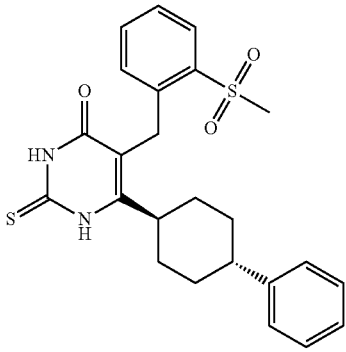 [SMILES: CS(=O)(=O)c1ccccc1Cc1c(=O)[nH]c(=S)[nH]c1[C@H]1CC[C@H](c2ccccc2)CC1] | (Method C)<br>$R_t$ = 3.48 min<br>$(M + H)^+$ = 455 |
| 12i | 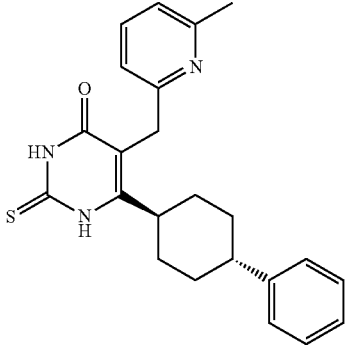 [SMILES: Cc1cccc(Cc2c(=O)[nH]c(=S)[nH]c2[C@H]2CC[C@H](c3ccccc3)CC2)n1] | (Method A)<br>$R_t$ = 2.46 min<br>$(M + H)^+$ = 392 |
| 12j | 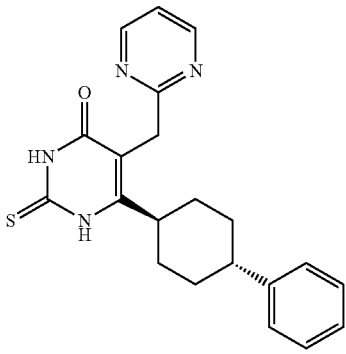 [SMILES: O=c1[nH]c(=S)[nH]c([C@H]2CC[C@H](c3ccccc3)CC2)c1Cc1ncccn1] | (Method A)<br>$R_t$ = 3.10 min<br>$(M + H)^+$ = 379 |

TABLE 4-continued

Substituted 2-thioxo-2,3-dihydro-pyrimidine-4-ones.

| Compound | Structure | LCMS |
|---|---|---|
| 12k | 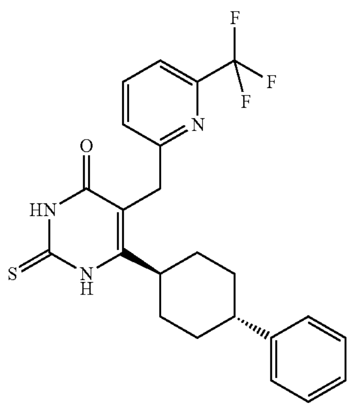 [SMILES: O=c1[nH]c(=S)[nH]c([C@H]2CC[C@H](c3ccccc3)CC2)c1Cc1cccc(C(F)(F)F)n1] | (Method C)<br>$R_t$ = 3.91 min<br>446 (M + H)$^+$ |
| 12l | | (Method A)<br>$R_t$ = 3.68 min<br>(M + H)$^+$ = 412/414 |
| 12m | 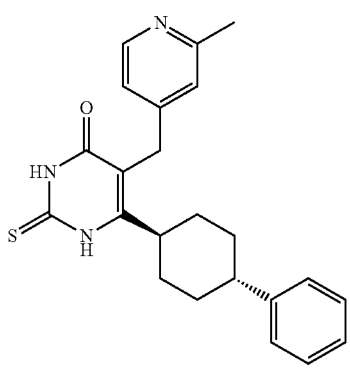 [SMILES: Cc1cc(Cc2c(=O)[nH]c(=S)[nH]c2[C@H]2CC[C@H](c3ccccc3)CC2)ccn1] | (Method C)<br>$R_t$ = 2.28 min<br>(M + H)$^+$ = 392 |
| 12n | 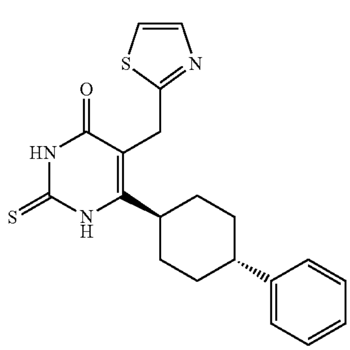 [SMILES: O=c1[nH]c(=S)[nH]c([C@H]2CC[C@H](c3ccccc3)CC2)c1Cc1nccs1] | (Method C)<br>$R_t$ = 3.33 min<br>(M + H)$^+$ = 384 |

TABLE 4-continued

Substituted 2-thioxo-2,3-dihydro-pyrimidine-4-ones.

| Compound | Structure | LCMS |
|---|---|---|
| 12o | 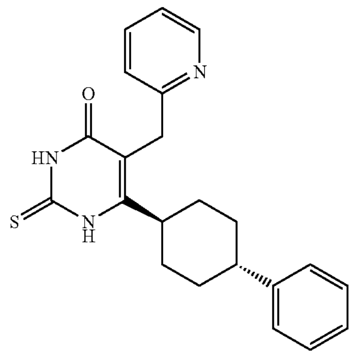 [SMILES: O=c1[nH]c(=S)[nH]c([C@H]2CC[C@H](c3ccccc3)CC2)c1Cc1ccccn1] | (Method C) $R_t$ = 2.54 min $(M + H)^+$ = 378 |
| 12p | 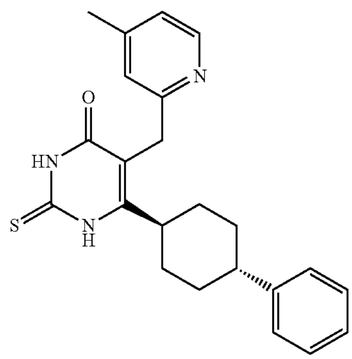 [SMILES: Cc1ccnc(Cc2c(=O)[nH]c(=S)[nH]c2[C@H]2CC[C@H](c3ccccc3)CC2)c1] | (Method C) $R_t$ = 2.41 min $(M + H)^+$ = 392 |
| 12q | 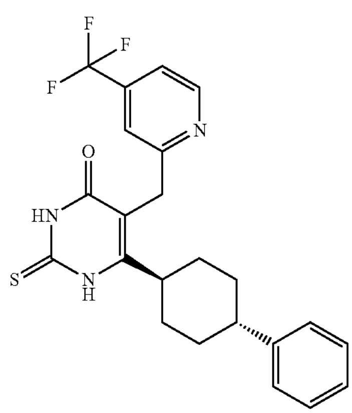 [SMILES: O=c1[nH]c(=S)[nH]c([C@H]2CC[C@H](c3ccccc3)CC2)c1Cc1cc(C(F)(F)F)ccn1] | (Method C) $R_t$ = 3.73 min $(M + H)^+$ = 384 |
| 12r | 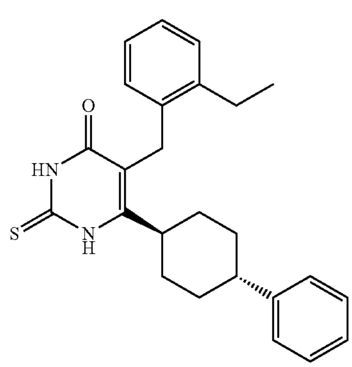 [SMILES: CCc1ccccc1Cc1c(=O)[nH]c(=S)[nH]c1[C@H]1CC[C@H](c2ccccc2)CC1] | (Method A) $R_t$ = 4.19 min $(M + H)^+$ = 405 |

TABLE 4-continued
Substituted 2-thioxo-2,3-dihydro-pyrimidine-4-ones.
| Compound | Structure | LCMS |
|---|---|---|
| 12s | 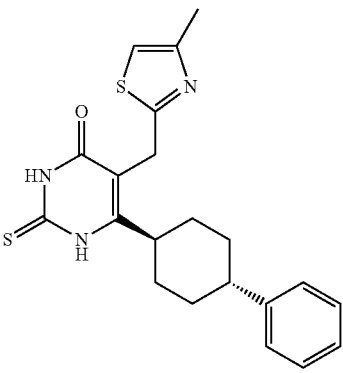 [SMILES: Cc1csc(Cc2c(=O)[nH]c(=S)[nH]c2[C@H]2CC[C@H](c3ccccc3)CC2)n1] | (Method A)<br>$R_t$ = 3.51 min<br>$(M + H)^+$ = 398 |
| 12t | 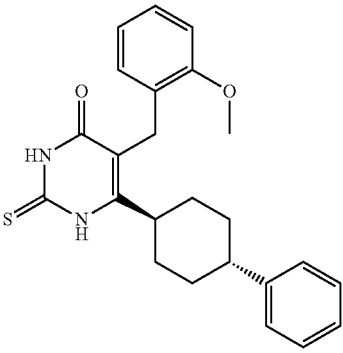 [SMILES: COc1ccccc1Cc1c(=O)[nH]c(=S)[nH]c1[C@H]1CC[C@H](c2ccccc2)CC1] | (Method A)<br>$R_t$ = 3.98 min<br>$(M + H)^+$ = 407 |
| 12u | 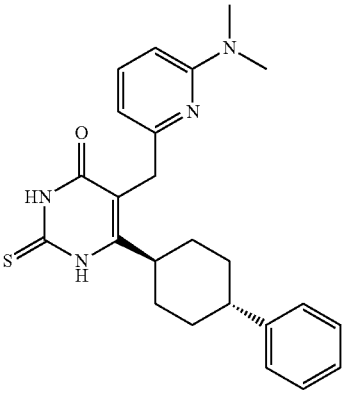 [SMILES: CN(C)c1cccc(Cc2c(=O)[nH]c(=S)[nH]c2[C@H]2CC[C@H](c3ccccc3)CC2)n1] | (Method C)<br>$R_t$ = 2.43 min<br>$(M + H)^+$ = 421 |
| 12v | 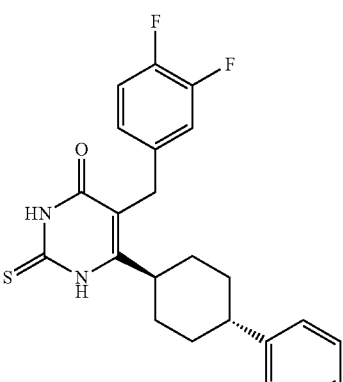 | (Method C)<br>$R_t$ = 3.90 min<br>$(M + H)^+$ = 413 |

TABLE 4-continued
Substituted 2-thioxo-2,3-dihydro-pyrimidine-4-ones.
| Compound | Structure | LCMS |
|---|---|---|
| 12w | 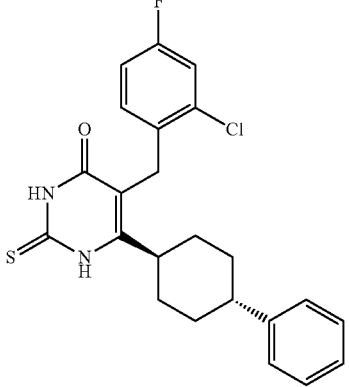 | (Method A)<br>$R_t$ = 4.19 min<br>$(M + H)^+$ = 429/431 |
| 12x | 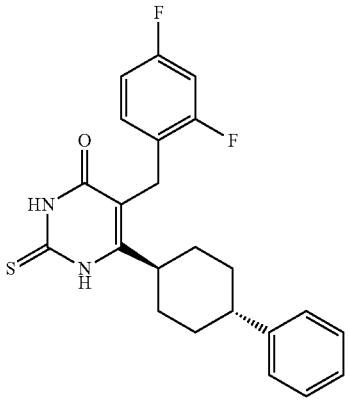 [SMILES: O=c1[nH]c(=S)[nH]c([C@H]2CC[C@H](c3ccccc3)CC2)c1Cc1ccc(F)cc1F] | (Method C)<br>$R_t$ = 3.96 min<br>$(M + H)^+$ = 413 |
| 12y | 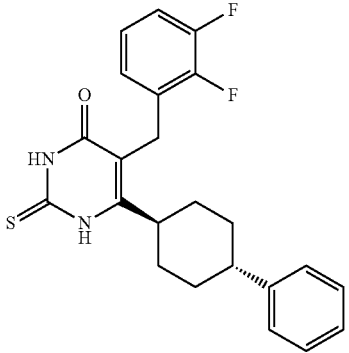 [SMILES: O=c1[nH]c(=S)[nH]c([C@H]2CC[C@H](c3ccccc3)CC2)c1Cc1cccc(F)c1F] | (Method A)<br>$R_t$ = 4.01 min<br>$(M + H)^+$ = 413 |

TABLE 4-continued

Substituted 2-thioxo-2,3-dihydro-pyrimidine-4-ones.

| Compound | Structure | LCMS |
|---|---|---|
| 12z | 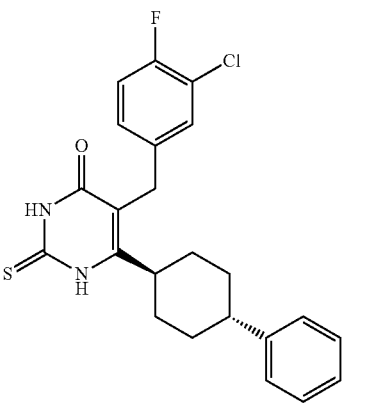 [SMILES: O=c1[nH]c(=S)[nH]c([C@H]2CC[C@H](c3ccccc3)CC2)c1Cc1ccc(F)c(Cl)c1] | (Method A) $R_t$ = 4.14 min $(M + H)^+$ = 429 |

Intermediates 12 were converted to Compounds 3 in Table 5 below, as for the preparation of compound 3b in Example 6.

TABLE 5

5-Substituted (E)-6-(4-cyclohexyl)-1H-pyrimidine-2,4-diones.

| Example | Compound | Structure | $^1$H NMR/δ | LCMS |
|---|---|---|---|---|
| 8 | 3a | (E)-5-Benzyl-6-(4-phenylcyclohexyl)-1H-pyrimidine-2,4-dione | (DMSO-d$_6$): 11.07 (1 H, s), 10.47 (1 H, s), 7.22-7.20 (10 H, m), 3.72 (2 H, s), 2.87-2.85 (1 H, m), 2.54-2.44 (1 H, m), 1.91-1.72 (4 H, m), 1.49-1.38 (4 H, m). | (Method B) $R_t$ = 4.94 min $(M + H)^+$ = 361 |
| 9 | 3c | (E)-5-(2-Chlorobenzyl)-6-(4-phenylcyclohexyl)-1H-pyrimidine-2,4-dione | (DMSO-d$_6$): 11.14 (1 H, s), 10.58 (1 H, s), 7.44 (1 H, dd, J = 7.47, 1.80 Hz), 7.22-7.21 (7 H, m), 7.08 (1 H, dd, J = 7.28, 2.13 Hz), 3.78 (2 H, s), 2.70-2.57 (1 H, m), 2.48-2.43 (1 H, m), 1.95-1.80 (2 H, m), 1.82-1.72 (2 H, m), 1.48 (2 H, d, J = 12.39 Hz), 1.39-1.35 (2 H, m). | (Method B) $R_t$ = 5.25 min $(M + H)^+$ = 395 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 10 | 3d | 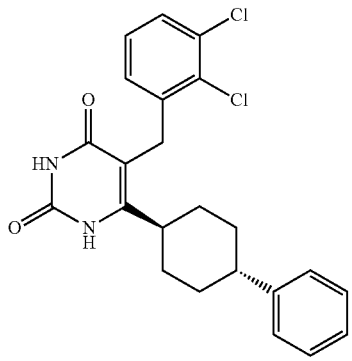<br>(E)-5-(2,3-Dichlorobenzyl)-6-(4-phenylcyclohexyl)-1H-pyrimidine-2,4-dione | (DMSO-$d_6$): 11.15 (1 H, s), 10.60 (1 H, s), 7.49 (1 H, dd, J = 7.98, 1.47 Hz), 7.26-7.25 (3 H, m), 7.19-7.17 (3 H, m), 7.05 (1 H, dd, J = 7.81, 1.45 Hz), 3.82 (2 H, s), 2.65-2.62 (1 H, m), 2.48-2.44 (1 H, m), 1.91-1.88 (2 H, m), 1.78-1.75 (2 H, m), 1.57-1.46 (2 H, m), 1.41-1.38 (2 H, m). | (Method B) $R_t$ = 5.53 min (M + H)$^+$ = 429 |
| 11 | 3e | 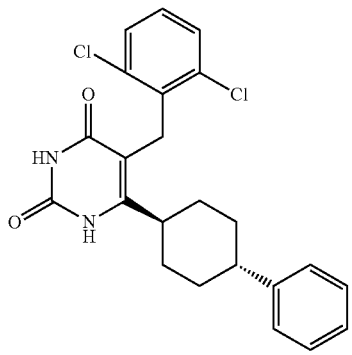 [SMILES: O=c1[nH]c(=O)c(Cc2c(Cl)cccc2Cl)c([C@H]2CC[C@H](c3ccccc3)CC2)[nH]1]<br>(E)-5-(2,6-Dichlorobenzyl)-6-(4-phenylcyclohexyl)-1H-pyrimidine-2,4-dione | (DMSO-$d_6$): 11.06 (1 H, s), 10.42 (1 H, s), 7.48 (2 H, d, J = 8.04 Hz), 7.28-7.27 (3 H, m), 7.15-7.14 (3 H, m), 4.03 (2 H, s), 2.47-2.39 (1 H, m), 1.75-1.71 (5 H, m), 1.15-1.11 (4 H, m). | (Method B) $R_t$ = 5.31 min (M + H)$^+$ = 429 |
| 12 | 3f | 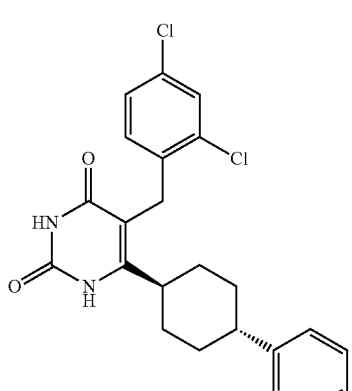<br>(E)-5-(2,4-Dichlorobenzyl)-6-(4-phenylcyclohexyl)-1H-pyrimidine-2,4-dione | (DMSO-$d_6$): 11.16 (1 H, s), 10.61 (1 H, s), 7.61 (1 H, d, J = 2.21 Hz), 7.36-7.23 (3 H, m), 7.20-7.14 (3 H, m), 7.10 (1 H, d, J = 8.42 Hz), 3.74 (2 H, s), 2.70-2.58 (1 H, m), 2.48-2.43 (1 H, m), 1.91-1.88 (2 H, m), 1.81-1.77 (2 H, m), 1.56-1.41 (2 H, m), 1.45-1.34 (2 H, m). | (Method B) $R_t$ = 5.68 min (M + H)$^+$ = 429 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 13 | 3g | (E)-5-(2,5-Dichlorobenzyl)-6-(4-phenylcyclohexyl)-1H-pyrimidine-2,4-dione | (DMSO-$d_6$): 11.15 (1 H, s), 10.61 (1 H, s), 7.50 (1 H, d, J = 8.53 Hz), 7.29-7.28 (3 H, m), 7.16-7.15 (4 H, m), 3.78 (2 H, s), 2.74-2.62 (1 H, m), 2.49-2.42 (1 H, m), 1.92-1.88 (2 H, m), 1.81-1.77 (2 H, m), 1.46-1.42 (4 H, m). | Method B $R_t$ = 5.45 min (M + H)$^+$ = 429 |
| 14 | 3i | (E)-5-(2-Methanesulfonylbenzyl)-6-(4-phenylcyclohexyl)-1H-pyrimidine-2,4-dione | (DMSO-$d_6$): 11.17 (1 H, s), 10.63 (1 H, s), 7.95 (1 H, dd, J = 7.92, 1.42 Hz), 7.61 (1 H, td, J = 7.58, 1.45 Hz), 7.47-7.45 (1 H, m), 7.26-7.24 (2 H, m), 7.18-7.16 (4 H, m), 4.14 (2 H, s), 3.37 (3 H, s), 2.83-2.79 (1 H, m), 2.47-2.44 (1 H, m), 1.89-1.86 (2 H, m), 1.80-1.70 (2 H, m), 1.56-1.46 (2 H, m), 1.47-1.34 (2 H, m). | (Method B) $R_t$ = 4.41 min (M + H)$^+$ = 439 |
| 15 | 3j | (E)-5-(6-Methylpyridin-2-ylmethyl)-6-(4-phenylcyclohexyl)-1H-pyrimidine-2,4-dione (isolated as hydrochloride) | (DMSO-$d_6$): 11.04 (1 H, s), 10.48 (1 H, s), 7.54 (1 H, t, J = 7.66 Hz), 7.31-7.24 (2 H, m), 7.23-7.15 (3 H, m), 7.03 (1 H, d, J = 7.60 Hz), 6.98 (1 H, d, J = 7.72 Hz), 3.79 (2 H, s), 3.11-3.03 (1 H, m), 2.58-2.52 (1 H, m), 2.41 (3 H, s), 1.84-1.83 (4 H, m), 1.60-1.48 (2 H, m), 1.53-1.41 (2 H, m). | (Method B) $R_t$ = 3.04 min (M + H)$^+$ = 376 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 16 | 3k | (E)-6-(4-Phenylcyclohexyl)-5-pyrimidin-2-ylmethyl-1H-pyrimidine-2,4-dione | (DMSO-d$_6$): 11.03 (1 H, s), 10.49 (1 H, s), 8.70 (2 H, d, J = 4.89 Hz), 7.28-7.27 (3 H, m), 7.19-7.17 (3 H, m), 4.02 (2 H, s), 2.80-2.77 (1 H, m), 2.49-2.44 (1 H, m), 1.85-1.82 (4 H, m), 1.50 (2 H, d, J = 12.32 Hz), 1.47-1.31 (2 H, m). | (Method B) R$_t$ = 3.73 min (M + H)$^+$ = 363 |
| 17 | 3l | (E)-5-(6-Trifluoromethylpyridin-2-ylmethyl)-6-(4-phenylcyclohexyl)-1H-pyrimidine-2,4-dione | (DMSO-d$_6$): 11.11 (1 H, s), 10.55 (1 H, s), 7.98 (1 H, t, J = 7.83 Hz), 7.70 (1 H, d, J = 7.69 Hz), 7.55 (1 H, d, J = 7.93 Hz), 7.28 (2 H, t, J = 7.48 Hz), 7.18-7.17 (4 H, m), 3.94 (2 H, s), 3.03 (1 H, s), 1.86-1.81 (4 H, m), 1.50 (4 H, dd, J = 33.29, 12.83 Hz). | |
| 18 | 3m | (E)-5-(3-Chloropyridin-2-ylmethyl)-6-(4-phenylcyclohexyl)-1H-pyrimidine-2,4-dione | (DMSO-d$_6$): 11.02 (1 H, s), 10.50 (1 H, s), 8.40 (1 H, dd, J = 4.66, 1.46 Hz), 7.89 (1 H, dd, J = 8.03, 1.47 Hz), 7.27-7.25 (3 H, m), 7.18-7.15 (3 H, m), 3.98 (2 H, s), 2.69-2.66 (1 H, m), 2.48-2.43 (1 H, m), 1.87-1.84 (2 H, m), 1.81-1.70 (2 H, m), 1.52-1.49 (2 H, m), 1.45-1.30 (2 H, m). | (Method B) R$_t$ = 4.57 min (M + H)$^+$ = 396 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 19 | 3n | (E)-5-(2-Methylpyridin-4-ylmethyl)-6-(4-phenylcyclohexyl)-1H-pyrimidine-2,4-dione | (DMSO-$d_6$): 11.11 (1 H, s), 10.53 (1 H, s), 8.28 (1 H, d, J = 5.14 Hz), 7.23-7.20 (5 H, m), 7.07 (1 H, s), 6.99 (1 H, d, J = 5.24 Hz), 3.69 (2 H, s), 2.82-2.74 (1 H, m), 2.55-2.50 (1 H, m), 2.40 (3 H, s), 1.95-1.75 (4 H, m), 1.49-1.45 (4 H, m). | (Method B) $R_t$ = 2.96 min $(M + H)^+$ = 376 |
| 20 | 3o | (E)-6-(4-Phenylcyclohexyl)-5-thiazol-2-ylmethyl-1H-pyrimidine-2,4-dione | (DMSO-$d_6$): 11.16 (1 H, s), 10.61 (1 H, s), 7.67 (1 H, d, J = 3.32 Hz), 7.52 (1 H, d, J = 3.32 Hz), 7.31-7.14 (5 H, m), 4.07 (2 H, s), 3.01-2.89 (1 H, m), 2.58-2.52 (1 H, m), 1.87-1.84 (4 H, m), 1.62-1.58 (2 H, m), 1.50-1.48 (2 H, m). | (Method B) $R_t$ = 4.09 min $(M + H)^+$ = 368 |
| 21 | 3p | (E)-5-(Pyridin-2-ylmethyl)-6-(4-phenylcyclohexyl)-1H-pyrimidine-2,4-dione | (DMSO-$d_6$): 11.07 (1 H, s), 10.49 (1 H, s), 8.45 (1 H, d, J = 4.89 Hz), 7.68 (1 H, td, J = 7.66, 1.88 Hz), 7.28 (2 H, m), 7.19-7.18 (5 H, m), 3.87 (2 H, s), 2.95 (1 H, m) 1.90-1.76 (4 H, m), 1.48-1.44 (4 H, m). | (Method B) $R_t$ = 3.11 minutes $(M + H)^+$ = 362 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 22 | 3q | (E)-5-(4-Methylpyridin-2-ylmethyl)-6-(4-phenylcyclohexyl)-1H-pyrimidine-2,4-dione | (DMSO-$d_6$): 11.04 (1 H, s), 10.47 (1 H, s), 8.28 (1 H, d, J = 5.02 Hz), 7.27 (2 H, m), 7.20-7.18 (3 H, m), 7.03-6.97 (2 H, m), 3.80 (2 H, s), 2.93 (1 H, s), 2.25 (3 H, s), 1.81 (4 H, m,), 1.46-1.42 (4 H, m), | (Method B) $R_t$ = 3.06 min (M + H)$^+$ = 376 |
| 23 | 3r | (E)-5-(4-Trifluoromethyl-methylpyridin-2-ylmethyl)-6-(4-phenylcyclohexyl)-1H-pyrimidine-2,4-dione | (DMSO-$d_6$): 11.08 (1 H, s), 10.53 (1 H, s), 8.73 (1 H, d, J = 5.14 Hz), 7.62 (1 H, s), 7.56 (1 H, d, J = 5.22 Hz), 7.27 (2 H, m), 7.19-7.17 (3 H, m), 3.99 (2 H, s), 2.91 (1 H, m), 1.90-1.79 (4 H, m), 1.45 (4 H, m). | (Method B) $R_t$ = 4.78 min (M + H)$^+$ = 430 |
| 24 | 3s | (E)-5-(2-Ethylbenzyl)-6-(4-phenylcyclohexyl)-1H-pyrimidine-2,4-dione | (DMSO-$d_6$): 11.08 (1 H, s), 10.52 (1 H, s), 7.27-7.25 (2 H, m), 7.16-7.15 (6 H, m), 6.91-6.87 (1 H, m), 3.70 (2 H, s), 2.72 (2 H, q, J = 7.51 Hz), 2.63-2.60 (1 H, m), 2.50-2.42 (1 H, m), 1.90-1.87 (2 H, m), 1.81-1.70 (2 H, m), 1.53-1.42 (2 H, m), 1.39-1.23 (2 H, m), 1.21 (3 H, t, J = 7.51 Hz). | (Method B) $R_t$ = 4.94 min (M + H)$^+$ = 361 |

TABLE 5-continued

5-Substituted (E)-6-(4-cyclohexyl)-1H-pyrimidine-2,4-diones.

| Example | Compound | Structure | $^1$H NMR/δ | LCMS |
|---------|----------|-----------|-------------|------|
| 25 | 3t | (E)-5-(4-Methylthiazol-2-ylmethyl)-6-(4-Phenylcyclohexyl)-1H-pyrimidine-2,4-dione | (DMSO-$d_6$): 11.15 (1 H, s), 10.61 (1 H, s), 7.27-7.15 (5 H, m), 7.03 (1 H, d, J = 1.12 Hz), 4.00 (2 H, s), 2.95 (1 H, m), 2.52 (1 H, m), 2.28 (3 H, d, J = 1.04 Hz) 1.87-1.83 (4 H, m), 1.54-1.51 (4 H, m). | (Method B) $R_t$ = 4.26 min $(M + H)^+$ = 382 |
| 26 | 3u | (E)-5-(2-Methoxybenzyl)-6-(4-phenylcyclohexyl)-1H-pyrimidine-2,4-dione | (DMSO-$d_6$): 11.07 (1 H, s), 10.49 (1 H, s), 7.27 (2 H, m), 7.17-7.16 (4 H, m), 6.97 (2 H, m), 6.84 (1 H, td, J = 7.42, 1.08 Hz), 3.86 (3 H, s), 3.64 (2 H, s), 2.74-2.71 (1 H, m), 1.83 (4 H,m), 1.40-1.37 (4 H, m). | (Method B) $R_t$ = 4.95 min $(M + H)^+$ |
| 27 | 3v | (E)-5-(6-Dimethylaminopyridin-2-yl)methyl-6-(4-phenylcyclohexyl)-1H-pyrimidine-2,4-dione | (DMSO-$d_6$): 11.00 (1 H, s), 10.40 (1 H, s), 7.36 (1 H, dd, J = 8.42, 7.29 Hz), 7.27 (2 H, m), 7.17 (3 H, m), 6.45-6.33 (2 H, m), 3.65 (2 H, s), 2.99 (6 H, s), 1.85-1.81 (4 H, m), 1.47 (4 H, m). | (Method B) $R_t$ = 3.22 min $(M + H)^+$ = 405 |

TABLE 5-continued

5-Substituted (E)-6-(4-cyclohexyl)-1H-pyrimidine-2,4-diones.

| Example | Compound | Structure | ¹H NMR/δ | LCMS |
|---|---|---|---|---|
| 28 | 3w | 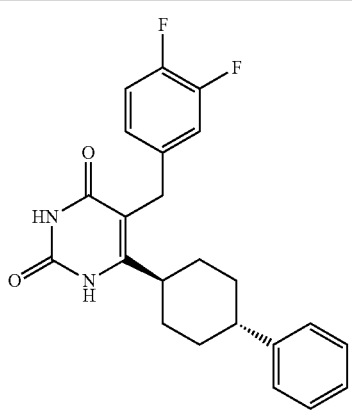 [SMILES: O=c1[nH]c(=O)c(Cc2ccc(F)c(F)c2)c([C@H]2CC[C@H](c3ccccc3)CC2)[nH]1]<br>(E)-5-(3,4-Difluorobenzyl)-6-(4-phenylcyclohexyl)-1H-pyrimidine-2,4-dione | (DMSO-d$_6$): 11.13 (1 H, s), 10.53 (1 H, s), 7.27-7.24 (7 H, m), 7.07 (1 H, s), 3.73 (2 H, s), 2.85 (1 H, m), 1.94-1.75 (4 H, m), 1.50-1.47 (4 H, m). | (Method B)<br>R$_t$ = 5.02 min<br>(M + H)$^+$ = 397 |
| 29 | 3x | 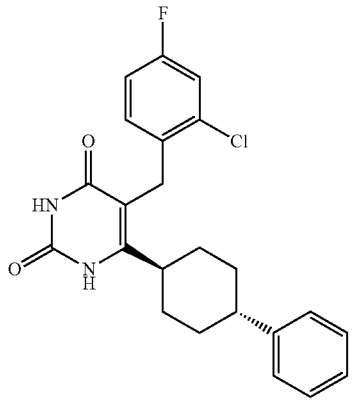<br>(E)-5-(2-Chloro-4-fluorobenzyl)-6-(4-phenylcyclohexyl)-1H-pyrimidine-2,4-dione | (DMSO-d$_6$): 11.16 (1 H, s), 10.61 (1 H, s), 7.45 (1 H, dt, J = 8.70, 1.44 Hz), 7.28 (2 H, m), 7.17-7.15 (5 H, m), 3.75 (2 H, s), 2.65 (1 H, t, J = 12.12 Hz), 1.87-1.84 (4 H, m), 1.57-1.34 (4 H, m). | (Method B)<br>R$_t$ = 5.33 min<br>(M + H)$^+$ = 413 |
| 30 | 3y | 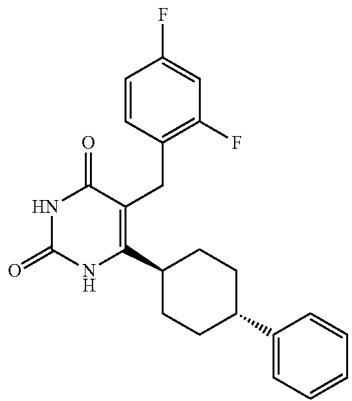 [SMILES: O=c1[nH]c(=O)c(Cc2ccc(F)cc2F)c([C@H]2CC[C@H](c3ccccc3)CC2)[nH]1]<br>(E)-5-(2,4-Difluorobenzyl)-6-(4-phenylcyclohexyl)-1H-pyrimidine-2,4-dione | (DMSO-d$_6$): 11.11 (1 H, s), 10.53 (1 H, s), 7.27 (2 H, m), 7.18 (5 H, m), 6.98 (1 H, td, J = 8.43, 2.67 Hz), 3.69 (2 H, s), 2.78 (1 H, t, J = 12.03 Hz), 1.88-1.85 (4 H, m), 1.47-1.44 (4 H, m). | (Method B)<br>R$_t$ = 5.09 min<br>(M + H)$^+$ = 397 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 31 | 3z | (E)-5-(2,3-Difluorobenzyl)-6-(4-phenylcyclohexyl)-1H-pyrimidine-2,4-dione | (DMSO-d$_6$): 11.12 (1 H, s), 10.56 (1 H, s), 7.21-7.19 (7 H, m), 6.97 (1 H, t, J = 7.16 Hz), 3.77 (2 H, s), 2.77 (1 H, m), 1.86-1.83 (4 H, m), 1.47 (4 H, m). | (Method B) R$_t$ = 5.05 min (M + H)$^+$ = 397 |
| 32 | 3aa | (E)-5-(3-Chloro-4-fluorobenzyl)-6-(4-phenylcyclohexyl)-1H-pyrimidine-2,4-dione | (DMSO-d$_6$): 11.11 (1 H, s), 10.53 (1 H, s), 7.45 (1 H, dd, J = 7.28, 2.14 Hz), 7.25-7.24 (7 H, m), 3.72 (2 H, s), 2.89 (1 H, m), 1.93-1.75 (4 H, m), 1.51-1.48 (4 H, m). | (Method B) R$_t$ = 5.22 min (M + H)$^+$ = 413 |
| 33 | 3bb | 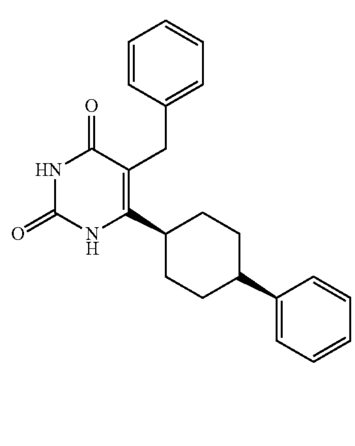 | (DMSO-d$_6$): 11.01 (1 H, s), 10.49 (1 H, s), 7.37-7.33 (2 H, m), 7.32-7.24 (4 H, m), 7.20-7.13 (4 H, m), 3.71 (2 H, s), 2.99 (1 H, br s) 2.85-2.74 (1 H, m), 2.17-2.03 (2 H, m), 1.82-1.66 (4 H, m), 1.27-1.14 (2 H, m). | (Method E) R$_t$ = 11.01 min (M + H)$^+$ = 361 |

TABLE 5-continued

5-Substituted (E)-6-(4-cyclohexyl)-1H-pyrimidine-2,4-diones.

| Example | Compound | Structure | $^1$H NMR/δ | LCMS |
|---|---|---|---|---|
| 34 | 3cc | 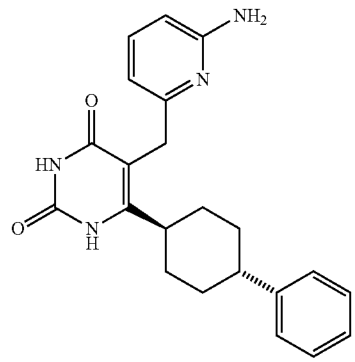 [SMILES: Nc1cccc(Cc2c(=O)[nH]c(=O)[nH]c2[C@H]2CC[C@H](c3ccccc3)CC2)n1] | (DMSO-$d_6$): 11.02 (1 H, s), 10.45 (1 H, s), 7.31-7.20 (5 H, m), 7.19-7.13 (1 H, m), 6.27-6.19 (2 H, m), 5.76 (2 H, s), 3.61 (2 H, s), 2.98-2.85 (1 H, m) 2.56-2.45 (1 H, m), 1.92-1.72 (4 H, m), 1.57-1.37 (4 H, m). | (Method D) $R_t$ = 3.00 min $(M + H)^+ = 377$ |

Example 35

(E)-3-Methyl-5-(3-methylbenzyl)-6-(4-phenylcyclohexyl)-1H-pyrimidine-2,4-dione (13a)

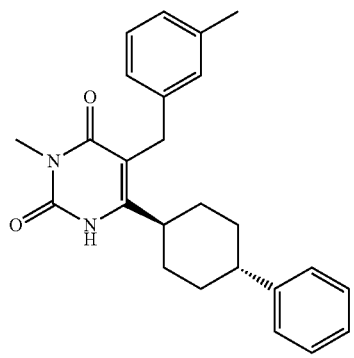 [SMILES: Cc1cccc(Cc2c(=O)n(C)c(=O)[nH]c2[C@H]2CC[C@H](c3ccccc3)CC2)c1]

(E)-3-Methyl-5-(3-methylbenzyl)-6-(4-phenylcyclohexyl)-1H-pyrimidine-2,4-dione (13a). Sodium hydride (2.1 mg; 0.053 mmol) was added to a solution of compound 3 h (20 mg; 0.053 mmol) in dry DMF (2 mL), followed by the addition of 3.3 μL (0.053 mmol) MeI The mixture was stirred at ambient temperature for 16 h. A further 1 eq. of NaH and MeI was added over the next 24 h. The contents were diluted with water (0.5 mL) and concentrated in vacuuo, and the resulting residue was purified by preparative LC (C18 column eluting with 30-95% $CH_3CN/H_2O$+0.1% formic acid), to give the titled product (13 mg) after freeze drying. $^1$H NMR δ (ppm) (DMSO-$d_6$): 10.76 (1H, s), 7.28 (2H, m), 7.18-7.17 (4H, m), 7.05-6.92 (3H, m), 3.74 (2H, s), 3.16 (3H, s), 2.90 (1H, s), 2.25 (3H, s), 1.90-1.78 (4H, m), 1.48 (4H, m). LCMS (Method B): $R_t$=5.56 minutes, $(M+H)^+$=389.

Examples 36-42

Preparation of 5-Substituted (E)-3-Alkyl-6-(4-cyclohexyl)-1H-pyrimidine-2,4-diones Example compounds in Table 6 below were prepared from appropriate compounds 3 with the requisite alkylating agents, such as described below for Examples 38-41. For related reactions describing alkylation of amines, see pages 397-408 of Larock, R. C. *Comprehensive Organic Transformations*. New York: VCH Publishers, Inc., 1989, the contents of which are herein incorporated by reference in their entirety.

TABLE 6

5-Substituted (E)-3-alkyl-6-(4-cyclohexyl)-1H-pyrimidine-2,4-diones.

| Example | Compound | Structure | NMR/δ | LCMS |
|---|---|---|---|---|
| 36 | 13b | 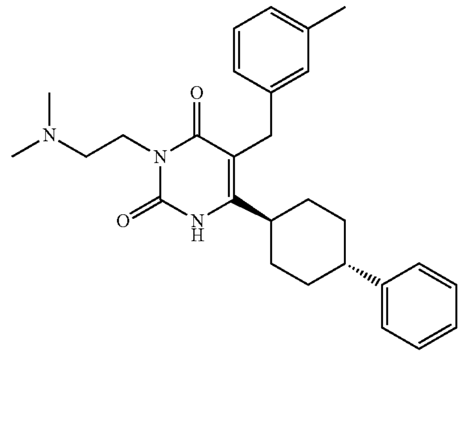 [SMILES: Cc1cccc(Cc2c(=O)n(CCN(C)C)c(=O)[nH]c2[C@H]2CC[C@H](c3ccccc3)CC2)c1] | (DMSO-$d_6$): 10.71 (1 H, s), 7.30-7.26 (2 H, m), 7.12-7.10 (4 H, m), 6.99-6.97 (3 H, m), 3.90 (2 H, t, J = 6.88 Hz), 3.73 (2 H, s), 2.89 (1 H, m), 2.41 (2 H, t, J = 6.88 Hz), 2.25 (3 H, s), 2.18 (6 H, s), 1.90-1.79 (4 H, m), 1.46 (4 H, m). | (Method B) $(M + H)^+ = 446$ |

TABLE 6-continued

5-Substituted (E)-3-alkyl-6-(4-cyclohexyl)-1H-pyrimidine-2,4-diones.

| Example | Compound | Structure | NMR/δ | LCMS |
|---|---|---|---|---|
| | | (E)-3-(2-Dimethylamino-ethyl)-5-(3-methyl-benzyl)-6-(4-phenyl-cyclohexyl)-1H-pyrimidine-2,4-dione | | |
| 37 | 13c | 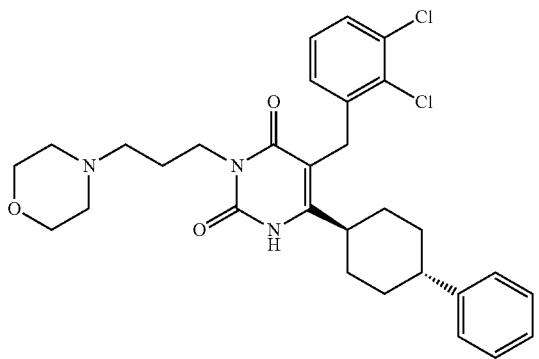 [SMILES: O=c1[nH]c([C@H]2CC[C@H](c3ccccc3)CC2)c(Cc2cccc(Cl)c2Cl)c(=O)n1CCCN1CCOCC1]<br>(E)-5-(2,3-Dichloro-benzyl)-3-(3-morpholin-4-yl-propyl)-6-(4-phenyl-cyclohexyl)-1H-pyrimidine-2,4-dione | (DMSO-d$_6$): 11.00 (1H, s), 9.96 (1H, s), 7.49 (1H, dd), 7.27 (3H, m), 7.17 (3H, m), 7.08 (1H, d), 3.96 (2H, d), 3.89 (2H, s) 3.85 (2H, t) 3.67 (2H, t) 3.40 (2H, d) 3.08 (4H, m) 2.71 (2H, t), 1.95 (4H, m), 1.79 (2H, d), 1.54 (2H, d), 1.43 (2H, m). | (Method B)<br>(M + H)$^+$ = 556 |
| 38 | 13d | 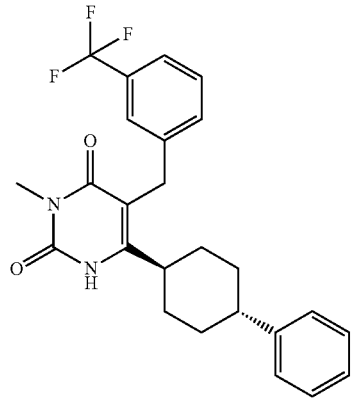 [SMILES: Cn1c(=O)[nH]c([C@H]2CC[C@H](c3ccccc3)CC2)c(Cc2cccc(C(F)(F)F)c2)c1=O]<br>(E)-3-Methyl-6-(4-phenyl-cyclohexyl)-5-(3-trifluoromethyl-benzyl)-1H-pyrimidine-2,4-dione | (DMSO-d$_6$): 10.82 (1 H, s), 7.63 (1 H, s), 7.55-7.45 (3H, m), 7.31-7.25 (2 H, m), 7.23-7.14 (3 H, m), 3.89 (2 H, s), 3.17 (3 H, s), 3.01-2.87 (1 H, m), 2.57-2.38 (1 H, m), 1.97-1.74 (4 H, m), 1.58-1.38 (4 H, m) | (Method D)<br>(M + H)$^+$ = 443 |
| 39 | 13e | 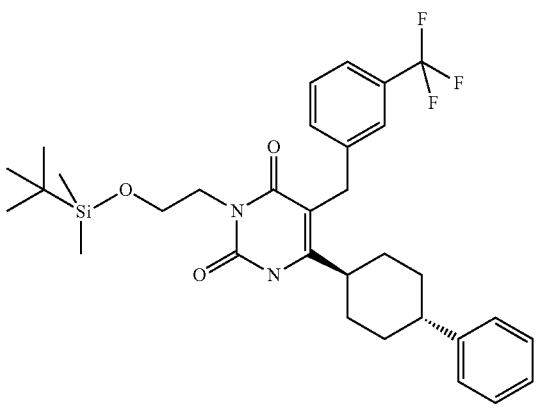 [SMILES: CC(C)(C)[Si](C)(C)OCCn1c(=O)[nH]c([C@H]2CC[C@H](c3ccccc3)CC2)c(Cc2cccc(C(F)(F)F)c2)c1=O]<br>(E)-3-[2-(tert-Butyl-dimethyl-silanyloxy)-ethyl]-6-(4-phenyl-cyclohexyl)-5-(3-trifluoromethyl-benzyl)-1H-pyrimidine-2,4-dione | (CDCl$_3$): 9.08 (1 H, s), 7.51-7.36 (4 H, m), 7.35-7.27 (2H, m), 7.25-7.15 (3 H, m), 4.18 (2 H, t, J = 6 Hz), 3.92-3.84 (4 H, m), 2.93-2.77 (1 H, m), 2.66-2.51 (1 H, m), 2.09-1.97 (2 H, m), 1.79-1.68 (4 H, m), 1.60-1.46 (2 H, m), 0.81 (9 H, s), −0.03 (6 H, s) | (Method A):<br>(M + H)$^+$ = 587 |

TABLE 6-continued

5-Substituted (E)-3-alkyl-6-(4-cyclohexyl)-1H-pyrimidine-2,4-diones.

| Example | Compound | Structure | NMR/δ | LCMS |
|---------|----------|-----------|-------|------|
| 40 | 13f | (E)-3-(2-Hydroxy-ethyl)-6-(4-phenyl-cyclohexyl)-5-(3-trifluoromethyl-benzyl)-1H-pyrimidine-2,4-dione | (DMSO-d$_6$): 10.77 (1 H, s), 7.63 (1 H, s), 7.54-7.49 (3 H, m), 7.31-7.25 (2 H, m), 7.22-7.14 (3 H, m), 4.75 (1 H, t, J = 5.9 Hz), 3.94-3.85 (4 H, m), 3.55-3.47 (2 H, m), 2.98-2.87 (1 H, m), 2.55-2.44 (1 H, m), 1.97-1.73 (4 H, m), 1.57-1.37 (4 H, m) | (Method D): (M + H)+ = 473 |
| 41 | 13g | (E)-3-(2-Methoxy-ethyl)-6-(4-phenyl-cyclohexyl)-5-(3-trifluoromethyl-benzyl)-1H-pyrimidine-2,4-dione | (DMSO-d$_6$): 10.81 (1 H, s), 7.62 (1 H, s), 7.55-7.47 (3 H, m), 7.31-7.25 (2 H, m), 7.23-7.14 (3 H, m), 4.00 (2 H, t), 3.88 (2 H, s), 3.50 (2 H, t, J = 6.7 Hz), 3.24 (3 H, s), 2.99-2.88 (1 H, m), 2.57-2.45 (1H, m), 1.97-1.73 (4 H, m), 1.57-1.38 (4 H, m) | (Method D): (M + H)$^+$ = 487 |
| 42 | 13h | 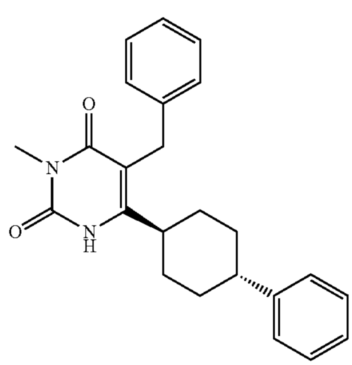 [SMILES: Cn1c(=O)[nH]c([C@H]2CC[C@H](c3ccccc3)CC2)c(Cc2ccccc2)c1=O] | (DMSO-d$_6$): 10.77 (1 H, s), 7.33-7.10 (10 H, m), 3.78 (2 H, s), 3.17 (3 H, s), 2.95-2.84 (1 H, m), 2.56-2.44 (1 H, m), 1.96-1.74 (4 H, m), 1.54-1.40 (4 H, m) | (Method D): (M + H)$^+$ = 375 |

Example 38

Preparation of (E)-3-Methyl-6-(4-phenyl-cyclohexyl)-5-(3-trifluoromethyl-benzyl)-1H-pyrimidine-2,4-dione (13d)

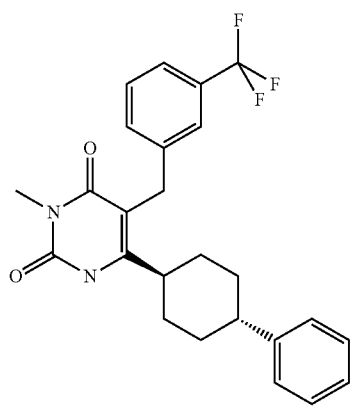 [SMILES: Cn1c(=O)[nH]c([C@H]2CC[C@H](c3ccccc3)CC2)c(Cc2cccc(C(F)(F)F)c2)c1=O]

Sodium hydride (6 mg; 0.14 mmol) was added to a solution of (E)-6-(4-phenyl-cyclohexyl)-5-(3-trifluoromethyl-benzyl)-1H-pyrimidine-2,4-dione (3b) (50 mg; 0.117 mmol) in dry DMF (3 mL), followed by the addition of 9 μL (0.14 mmol) methyl iodide after 30 minutes. The reaction mixture was stirred at ambient temperature for 18 hours. A further 0.2 equivalents of NaH and MeI was added and stirring continued for 2 hours and 25 minutes. Then the contents were diluted with water (10 mL). The mixture was extracted with ethyl acetate (2×20 mL) and the organic phases were dried (Na$_2$SO$_4$), filtered and evaporated. The residue was recrystallised out of boiling methanol to afford the product, 10.2 mg. R$_t$=5.63 minutes.

Example 39

Preparation of (E)-3-[2-(tert-Butyl-dimethyl-silanyloxy)-ethyl]-6-(4-phenyl-cyclohexyl-5-(3-trifluoromethyl-benzyl-1H-pyrimidine-2,4-dione (13e)

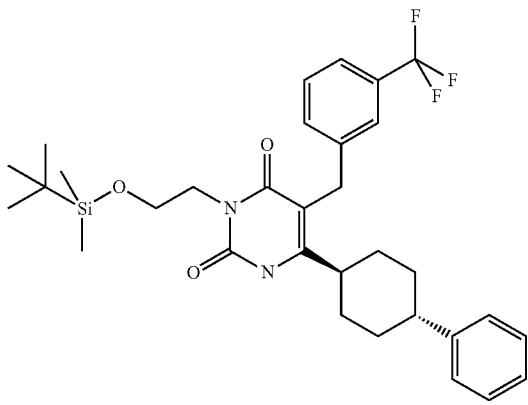 [SMILES: CC(C)(C)[Si](C)(C)OCCn1c(=O)[nH]c([C@H]2CC[C@H](c3ccccc3)CC2)c(Cc2cccc(C(F)(F)F)c2)c1=O]

Sodium hydride (18 mg; 0.46 mmol) was added to a solution of (E)-6-(4-phenyl-cyclohexyl)-5-(3-trifluoromethyl-benzyl)-1H-pyrimidine-2,4-dione (3b) (150 mg; 0.35 mmol) in dry DMF (5 mL), followed by the addition of 9 μL (0.14 mmol) of (2-bromo-ethoxy)-tert-butyl-dimethyl-silane after 25 minutes at 80° C. The reaction mixture was stirred at 80° C. for 18 h. A further 2.5 equivalents of NaH and MeI were added over 24 hours. The reaction mixture was diluted with water (10 mL) and extracted with ethyl acetate (4×10 mL) then the organic phase was dried (Na$_2$SO$_4$), filtered and evaporated. The material was purified by column chromatography eluting with a mixture of ethyl acetate and cyclohexane (0:1 to 1:0 by volume) to afford the title compound, 57 mg. R$_t$=5.09 minutes.

Example 40

Preparation of (E)-3-(2-Hydroxy-ethyl)-6-(4-phenyl-cyclohexyl)-5-(3-trifluoromethyl-benzyl)-1H-pyrimidine-2,4-dione (13f)

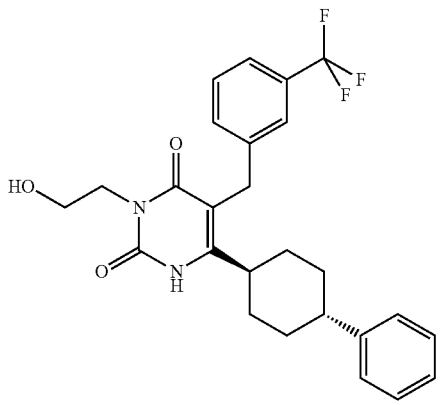 [SMILES: O=c1[nH]c([C@H]2CC[C@H](c3ccccc3)CC2)c(Cc2cccc(C(F)(F)F)c2)c(=O)n1CCO]

Tetrabutylammonium fluoride (1M in THF, 141 μL; 0.141 mmol) was added to a stirring solution of (E)-3-[2-(tert-butyl-dimethyl-silanyloxy)-ethyl]-6-(4-phenyl-cyclohexyl)-5-(3-trifluoromethyl-benzyl)-1H-pyrimidine-2,4-dione (13f) (55 mg; 0.094 mmol) in THF (5 mL). The reaction mixture was stirred for 1 hour then left to stand for 5 days. Water (10 mL) was added and the mixture was extracted with diethyl ether (2×10 mL). The organics were dried (Na$_2$SO$_4$), filtered and evaporated. The material was purified by column chromatog-

Example 41

Preparation of (E)-3-(2-Methoxy-ethyl)-6-(4-phenyl-cyclohexyl)-5-(3-trifluoromethyl-benzyl)-1H-pyrimidine-2,4-dione (13a)

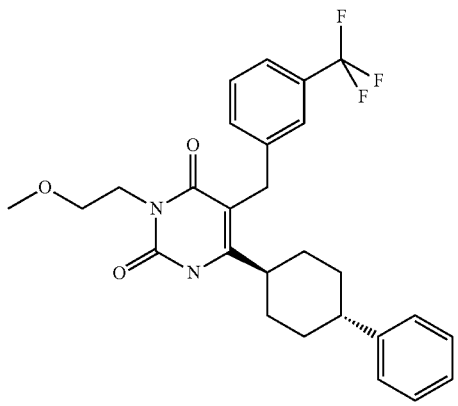 [SMILES: COCCn1c(=O)[nH]c([C@H]2CC[C@H](c3ccccc3)CC2)c(Cc2cccc(C(F)(F)F)c2)c1=O]

Sodium hydride (13 mg; 0.316 mmol) was added to a solution of (E)-6-(4-phenyl-cyclohexyl)-5-(3-trifluoromethyl-benzyl)-1H-pyrimidine-2,4-dione (3b) (104 mg; 0.243 mmol) in dry DMF (4 mL), followed by the addition of 30 μL (0.316 mmol) of 1-bromo-2-methoxyethane after 30 minutes. The reaction mixture was stirred at 80° C. for 42 hours. The reaction mixture was diluted with water (10 mL) and extracted with ethyl acetate (3×10 mL) then the organic phases were dried ($Na_2SO_4$), filtered and evaporated. The material was purified by column chromatography eluting with a mixture of ethyl acetate and cyclohexane (0:1 to 1:0 by volume) then further purified by preparative LC (C18 column eluting with 10-98% $CH_3CN/H_2O$+0.1% formic acid, to give the product, 7 mg after freeze drying. Rt=5.70 minutes.

Example 43

Glucocorticoid Receptor Binding Assay

The following is a description of an assay for determining the inhibition of dexamethasone binding of the Human Recombinant Glucocorticoid Receptor:

Binding protocol: Compounds were tested in a binding displacement assay using human recombinant glucocorticoid receptor with $^3$H-dexamethasone as the ligand. The source of the receptor was recombinant baculovirus-infected insect cells. This GR was a full-length steroid hormone receptor likely to be associated with heat-shock and other endogenous proteins.

The assay was carried out in v-bottomed 96-well polypropylene plates in a final volume of 100 μl containing 0.5 nM GR solution, 2.5 nM 3H-dexamethasone (Perkin Elmer NET 119200) in presence of test compounds, test compound vehicle (for total binding) or excess dexamethasone (20 μM, to determine non-specific binding) in an appropriate volume of assay buffer.

For the $IC_{50}$ determinations, test compounds were tested at 6 concentrations in duplicate. Test compounds were diluted from 10 mM stock in 100% DMSO. The tested solutions were prepared at 2× final assay concentration in 2% DMSO/assay buffer.

All reagents and the assay plate were kept on ice during the addition of reagents. The reagents were added to wells of a v-bottomed polypropylene plate in the following order: 25 μl of 10 nM 3H-dexamethasone solution, 50 μl of TB/NSB/compound solution and 25 μl of 2 nM GR solution. After the additions, the incubation mixture was mixed and incubated for 2.5 hrs at 4° C.

After 2.5 hrs incubation, unbound counts were removed with dextran coated charcoal (DCC) as follows: 15 μl of DCC solution (10% DCC in assay buffer) was added to all wells and mixed (total volume 115 μl). The plate was centrifuged at 4000 rpm for 10 minutes at 4° C. 75 μl of the supernatants was carefully pipetted into an optiplate. 150 μl of scintillation cocktail were added (Microscint-40, Perkin Elmer). The plate was vigorously shaken for approx. 10 minutes and counted on Topcount.

For the $IC_{50}$ determinations, the results were calculated as % inhibition [$^3$H]-dexamethasone bound and fitted to sigmoidal curves (fixed to 100 and 0) to obtain $IC_{50}$ values (concentration of compound that displaces 50% of the bound counts). The $IC_{50}$ values were converted to $K_i$ (the inhibition constant) using the Cheng-Prusoff equation. Test results are presented in Table 7.

Reagents: Assay buffer. 10 mM potassium phosphate buffer pH 7.6 containing 5 mM DTT, 10 mM sodium molybdate, 100 μM EDTA and 0.1% BSA.

Example 44

GR Functional Assay Using SW1353/MMTV-5 Cells

SW1353/MMTV-5 is an adherent human chondrosarcoma cell line that contains endogenous glucocorticoid receptors. It was transfected with a plasmid (pMAMneo-Luc) encoding firefly luciferase located behind a glucocorticoid-responsive element (GRE) derived from a viral promoter (long terminal repeat of mouse mammary tumor virus). A stable cell line SW1353/MMTV-5 was selected with geneticin, which was required to maintain this plasmid. This cell line was thus sensitive to glucocorticoids (dexamethasone) leading to expression of luciferase ($EC_{50}^{dex}$10 nM). This dexamethasone-induced response was gradually lost over time, and a new culture from an earlier passage was started (from a cryostored aliquot) every three months.

In order to test for a GR-antagonist, SW1353/MMTV-5 cells were incubated with several dilutions of the compounds in the presence of 5×$EC_{50}^{dex}$ (50 nM), and the inhibition of induced luciferase expression was measured using luminescence detected on a Topcount (Britelite Plus kit, Perking Elmer). For each assay, a dose-response curve for dexamethasone was prepared in order to determine the $EC_{50}^{dex}$ required for calculating the $K_i$ from the $IC_{50}$'s of each tested compound.

SW1353/MMTV-5 cells were distributed in 96-well plates and incubated in medium (without geneticin) for 24 hrs. Dilutions of the compounds in medium+50 nM dexamethasone were added and the plates further incubated for another 24 hrs after which the luciferase expression is measured.

TABLE 7

Activity data for selected compounds.

| Compound | Structure | GR Binding $K_i$ | GR Functional $K_i$ |
|---|---|---|---|
| 2a | 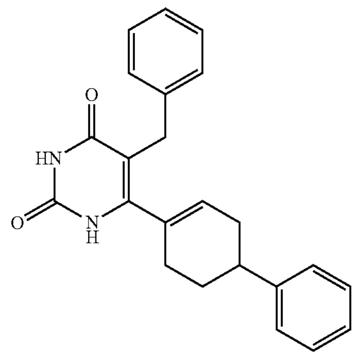 [SMILES: O=c1[nH]c(C2=CCC(c3ccccc3)CC2)c(Cc2ccccc2)c(=O)[nH]1] | + | + |
| 2b | 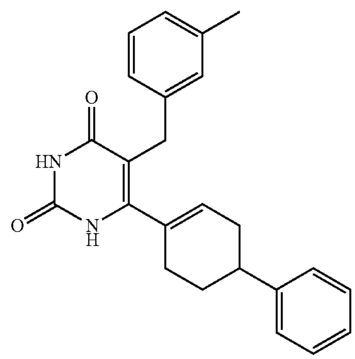 [SMILES: Cc1cccc(Cc2c(C3=CCC(c4ccccc4)CC3)[nH]c(=O)[nH]c2=O)c1] | ++ | ++ |
| 2c | 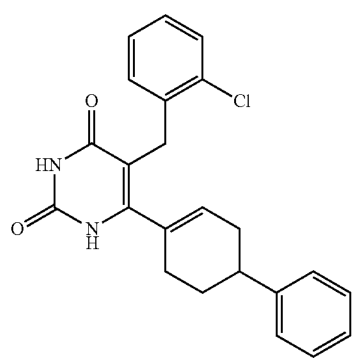 [SMILES: O=c1[nH]c(C2=CCC(c3ccccc3)CC2)c(Cc2ccccc2Cl)c(=O)[nH]1] | ++ | + |
| 2d | 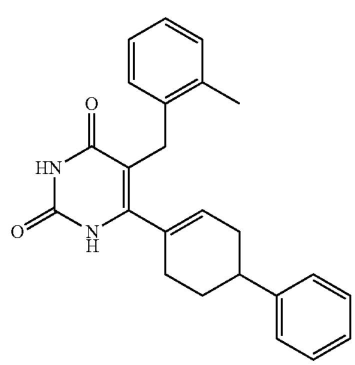 [SMILES: Cc1ccccc1Cc1c(C2=CCC(c3ccccc3)CC2)[nH]c(=O)[nH]c1=O] | + | + |

TABLE 7-continued

Activity data for selected compounds.

| Compound | Structure | GR Binding $K_i$ | GR Functional $K_i$ |
| --- | --- | --- | --- |
| 3a | 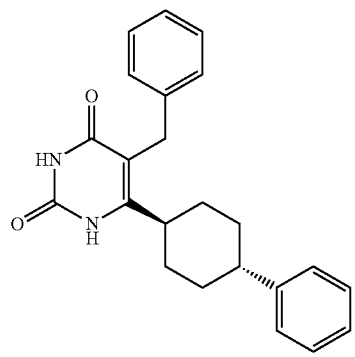 [SMILES: O=c1[nH]c(=O)c(Cc2ccccc2)c([C@H]2CC[C@H](c3ccccc3)CC2)[nH]1] | +++ | +++ |
| 3b | 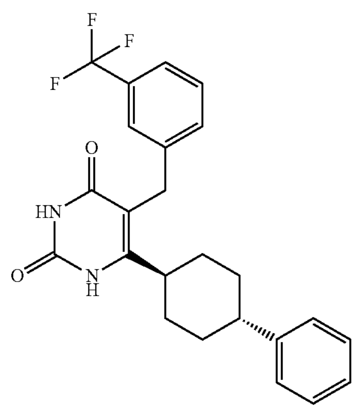 [SMILES: O=c1[nH]c(=O)c(Cc2cccc(C(F)(F)F)c2)c([C@H]2CC[C@H](c3ccccc3)CC2)[nH]1] | ++ | +++ |
| 3c | 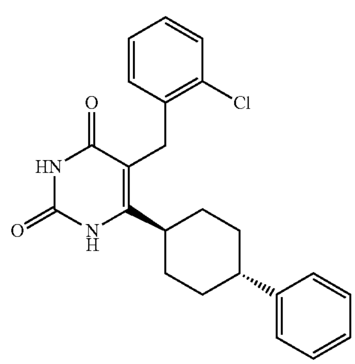 [SMILES: O=c1[nH]c(=O)c(Cc2ccccc2Cl)c([C@H]2CC[C@H](c3ccccc3)CC2)[nH]1] | +++ | +++ |
| 3d | 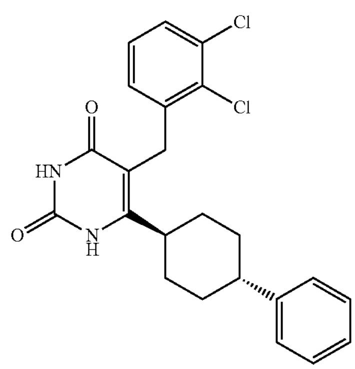 | +++ | +++ |

TABLE 7-continued

Activity data for selected compounds.

| Compound | Structure | GR Binding $K_i$ | GR Functional $K_i$ |
|---|---|---|---|
| 3e | 2,6-dichlorobenzyl substituted pyrimidine-2,4-dione with trans-4-phenylcyclohexyl | ++ | ++ |
| 3f | 2,4-dichlorobenzyl substituted pyrimidine-2,4-dione with trans-4-phenylcyclohexyl | ++ | +++ |
| 3g | 2,5-dichlorobenzyl substituted pyrimidine-2,4-dione with trans-4-phenylcyclohexyl | +++ | +++ |
| 3h | 3-methylbenzyl substituted pyrimidine-2,4-dione with trans-4-phenylcyclohexyl | +++ | +++ |

TABLE 7-continued

Activity data for selected compounds.

| Compound | Structure | GR Binding $K_i$ | GR Functional $K_i$ |
|---|---|---|---|
| 3j | 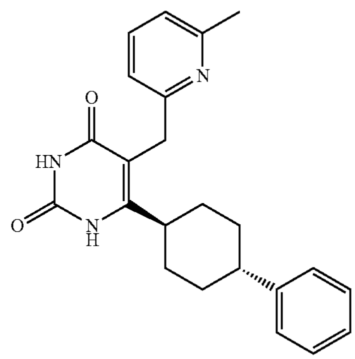 [SMILES: Cc1cccc(Cc2c(=O)[nH]c(=O)[nH]c2[C@H]2CC[C@H](c3ccccc3)CC2)n1] | + | ++ |
| 3k | 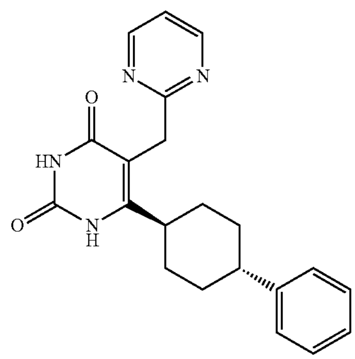 [SMILES: O=c1[nH]c(=O)c(Cc2ncccn2)c([C@H]2CC[C@H](c3ccccc3)CC2)[nH]1] | + | + |
| 3l | 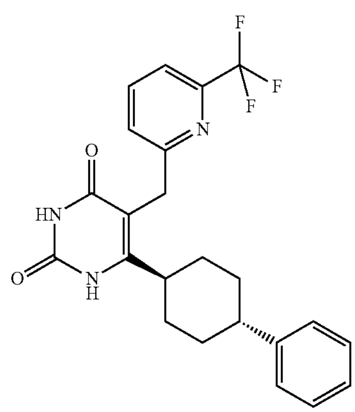 [SMILES: O=c1[nH]c(=O)c(Cc2cccc(C(F)(F)F)n2)c([C@H]2CC[C@H](c3ccccc3)CC2)[nH]1] | ++ | +++ |
| 3m | 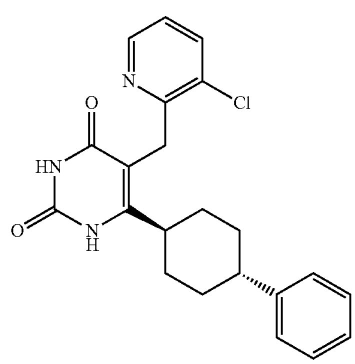 [SMILES: O=c1[nH]c(=O)c(Cc2ncccc2Cl)c([C@H]2CC[C@H](c3ccccc3)CC2)[nH]1] | + | + |

TABLE 7-continued

Activity data for selected compounds.

| Compound | Structure | GR Binding $K_i$ | GR Functional $K_i$ |
|---|---|---|---|
| 3n | 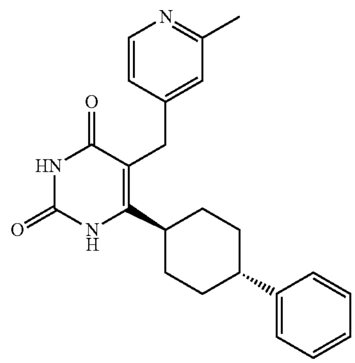 [SMILES: Cc1cc(Cc2c(=O)[nH]c(=O)[nH]c2[C@H]2CC[C@H](c3ccccc3)CC2)ccn1] | + | — |
| 3o | 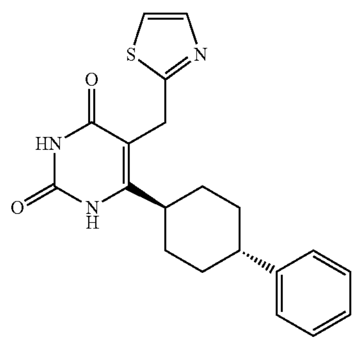 [SMILES: O=c1[nH]c(=O)c(Cc2nccs2)c([C@H]2CC[C@H](c3ccccc3)CC2)[nH]1] | + | + |
| 3p | 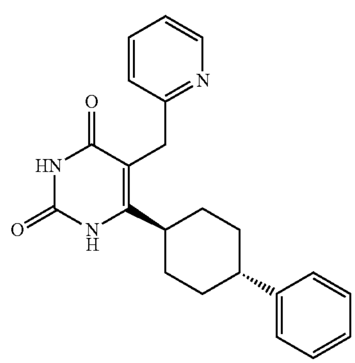 [SMILES: O=c1[nH]c(=O)c(Cc2ccccn2)c([C@H]2CC[C@H](c3ccccc3)CC2)[nH]1] | + | + |
| 3q | 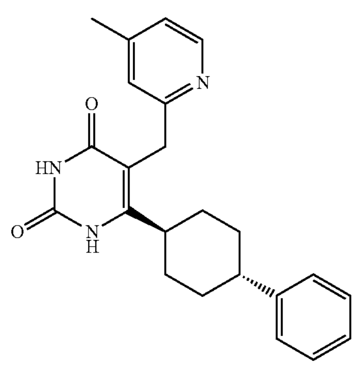 [SMILES: Cc1ccnc(Cc2c(=O)[nH]c(=O)[nH]c2[C@H]2CC[C@H](c3ccccc3)CC2)c1] | + | +++ |

TABLE 7-continued

Activity data for selected compounds.

| Compound | Structure | GR Binding $K_i$ | GR Functional $K_i$ |
|---|---|---|---|
| 3r | 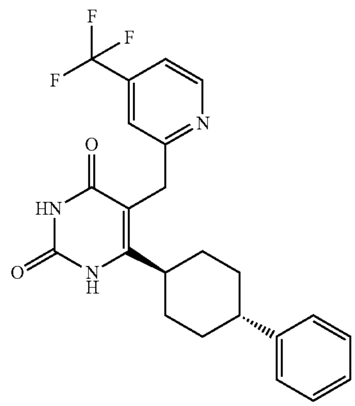 [SMILES: O=c1[nH]c(=O)c(Cc2cc(C(F)(F)F)ccn2)c([C@H]2CC[C@H](c3ccccc3)CC2)[nH]1] | + | ++ |
| 3s | 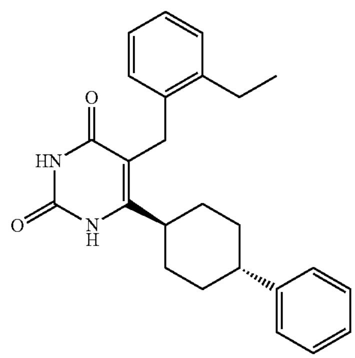 [SMILES: CCc1ccccc1Cc1c(=O)[nH]c(=O)[nH]c1[C@H]1CC[C@H](c2ccccc2)CC1] | ++ | ++ |
| 3t | 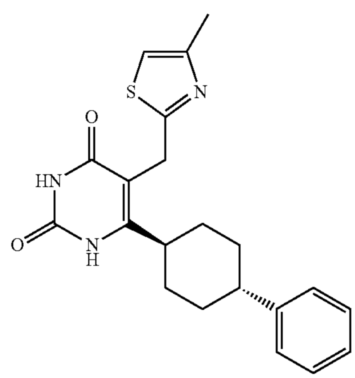 [SMILES: Cc1csc(Cc2c(=O)[nH]c(=O)[nH]c2[C@H]2CC[C@H](c3ccccc3)CC2)n1] | + | + |
| 3u | 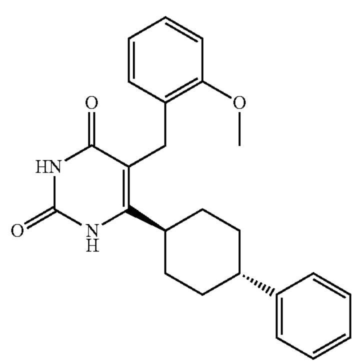 [SMILES: COc1ccccc1Cc1c(=O)[nH]c(=O)[nH]c1[C@H]1CC[C@H](c2ccccc2)CC1] | +++ | ++ |

TABLE 7-continued

Activity data for selected compounds.

| Compound | Structure | GR Binding $K_i$ | GR Functional $K_i$ |
|---|---|---|---|
| 3v | 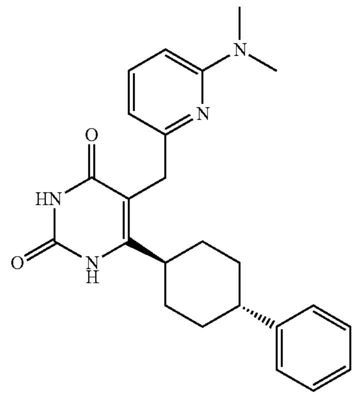 [SMILES: CN(C)c1cccc(Cc2c(=O)[nH]c(=O)[nH]c2[C@H]2CC[C@H](c3ccccc3)CC2)n1] | ++ | +++ |
| 3w | 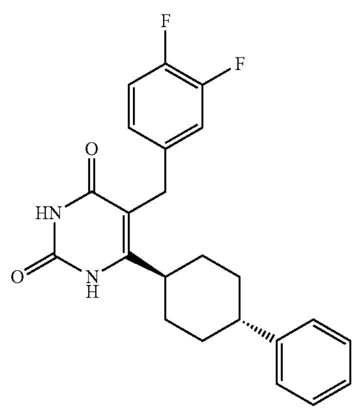 [SMILES: O=c1[nH]c(=O)c(Cc2ccc(F)c(F)c2)c([C@H]2CC[C@H](c3ccccc3)CC2)[nH]1] | + | ++ |
| 3x | 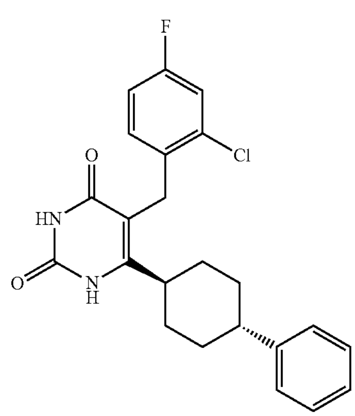 [SMILES: O=c1[nH]c(=O)c(Cc2ccc(F)cc2Cl)c([C@H]2CC[C@H](c3ccccc3)CC2)[nH]1] | + | +++ |

TABLE 7-continued

Activity data for selected compounds.

| Compound | Structure | GR Binding $K_i$ | GR Functional $K_i$ |
|---|---|---|---|
| 3y | 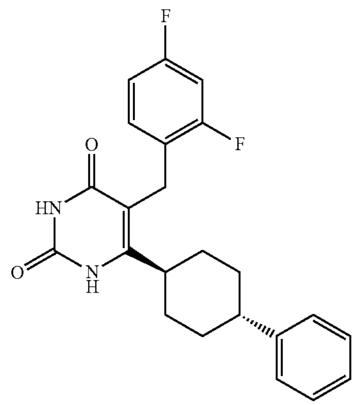 [SMILES: O=c1[nH]c(=O)c(Cc2ccc(F)cc2F)c([C@H]2CC[C@H](c3ccccc3)CC2)[nH]1] | ++ | ++ |
| 3z | 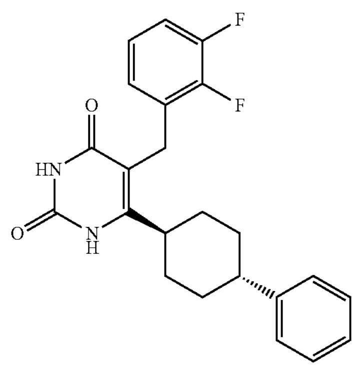 [SMILES: O=c1[nH]c(=O)c(Cc2cccc(F)c2F)c([C@H]2CC[C@H](c3ccccc3)CC2)[nH]1] | +++ | +++ |
| 3aa | 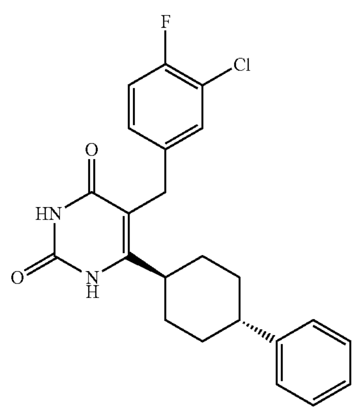 | + | +++ |
| 3bb | 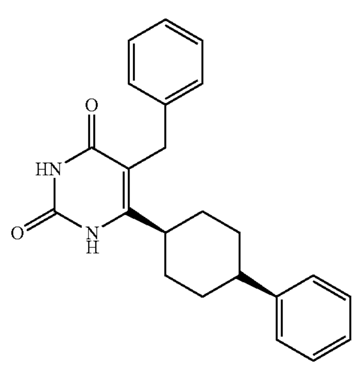 | + | — |

TABLE 7-continued

Activity data for selected compounds.

| Compound | Structure | GR Binding $K_i$ | GR Functional $K_i$ |
|---|---|---|---|
| 12g | 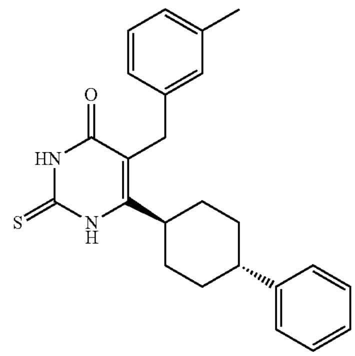 [SMILES: Cc1cccc(Cc2c(=O)[nH]c(=S)[nH]c2[C@H]2CC[C@H](c3ccccc3)CC2)c1] | + | + |
| 13a | 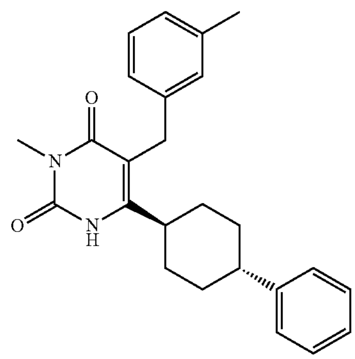 [SMILES: Cc1cccc(Cc2c(=O)n(C)c(=O)[nH]c2[C@H]2CC[C@H](c3ccccc3)CC2)c1] | ++ | +++ |
| 13b | 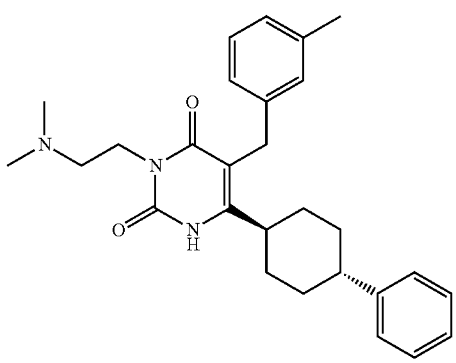 [SMILES: Cc1cccc(Cc2c(=O)n(CCN(C)C)c(=O)[nH]c2[C@H]2CC[C@H](c3ccccc3)CC2)c1] | + | + |
| 13c | 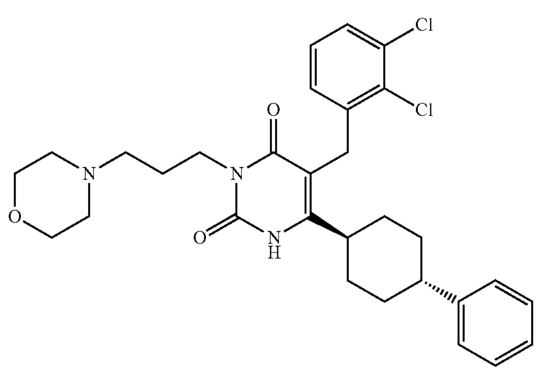 [SMILES: O=c1[nH]c([C@H]2CC[C@H](c3ccccc3)CC2)c(Cc2cccc(Cl)c2Cl)c(=O)n1CCCN1CCOCC1] | + | + |

TABLE 7-continued

Activity data for selected compounds.

| Compound | Structure | GR Binding $K_i$ | GR Functional $K_i$ |
|---|---|---|---|
| 13d | 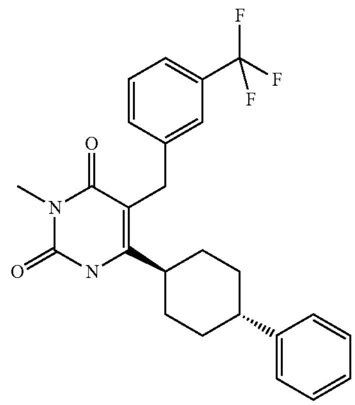 [SMILES: Cn1c(=O)[nH]c([C@H]2CC[C@H](c3ccccc3)CC2)c(Cc2cccc(C(F)(F)F)c2)c1=O] | ++ | + |
| 13f | 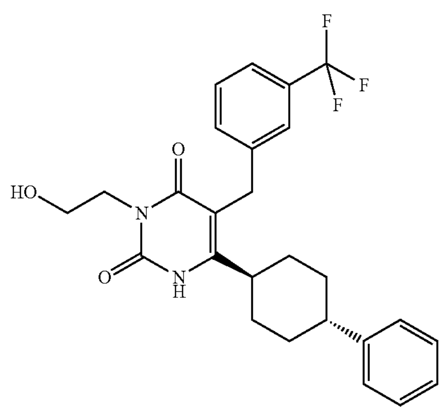 [SMILES: O=c1[nH]c([C@H]2CC[C@H](c3ccccc3)CC2)c(Cc2cccc(C(F)(F)F)c2)c(=O)n1CCO] | + | + |
| 13g | 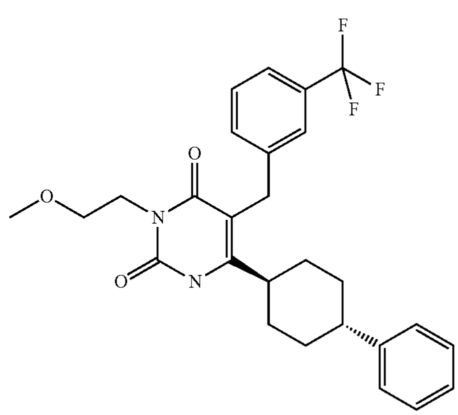 [SMILES: COCCn1c(=O)[nH]c([C@H]2CC[C@H](c3ccccc3)CC2)c(Cc2cccc(C(F)(F)F)c2)c1=O] | + | + |

TABLE 7-continued

Activity data for selected compounds.

| Compound | Structure | GR Binding $K_i$ | GR Functional $K_i$ |
|---|---|---|---|
| 3cc | 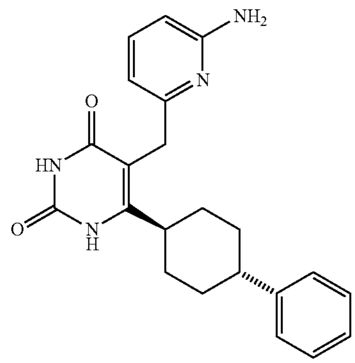 [SMILES: Nc1cccc(Cc2c(=O)[nH]c(=O)[nH]c2[C@H]2CC[C@H](c3ccccc3)CC2)n1] | + | + |
| 13h | 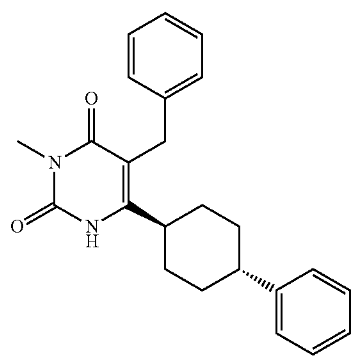 [SMILES: Cn1c(=O)[nH]c([C@H]2CC[C@H](c3ccccc3)CC2)c(Cc2ccccc2)c1=O] | + | ++ |

In Table 7, GR Binding compounds with a $K_i$ value of less than 5.0 nM are designated with +++; compounds with a $K_i$ value of 5.0 nM to 10.0 nM are designated with ++; and compounds with a $K_i$ value greater than 10 nM are designated with +. GR Functional compounds with a $K_i$ value of less than 50 nM are designated with +++, compounds with a $K_i$ value of 50 nM to 100 nM are designated with ++; and compounds with a $K_i$ value greater than 100 nM are designated with +.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula Ic:

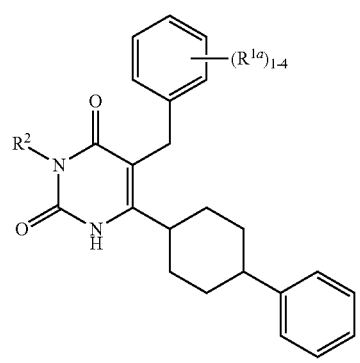

(Ic)

wherein
- each $R^{1a}$ is independently selected from the group consisting of H, $C_{1-6}$ alkyl, $C_{1-6}$ alkoxy, halogen, $C_{1-6}$ haloalkyl, $-NR^{1b}R^{1c}$, and $-SO_2R^{1b}$;
- $R^{1b}$ and $R^{1c}$ are each independently selected from the group consisting of H and $C_{1-6}$ alkyl; and
- $R^2$ is selected from the group consisting of H and $C_{1-6}$ alkyl;
- and salts and isomers thereof.

2. The compound of claim 1, wherein each $R^{1a}$ is $C_{1-6}$ haloalkyl.

3. The compound of claim 1, wherein each $R^{1a}$ is independently selected from the group consisting of H, Me, Et, —OMe, F, Cl, —$CF_3$, —$NMe_2$, and —$SO_2Me$.

4. The compound of claim 1, wherein each $R^{1a}$ is —$CF_3$.

5. The compound of claim 1, wherein $R^2$ is H.

6. A pharmaceutical composition comprising a pharmaceutically acceptable excipient and a compound of claim 1.

* * * * *